US011273170B2

(12) United States Patent
Leong

(10) Patent No.: US 11,273,170 B2
(45) Date of Patent: Mar. 15, 2022

(54) METHODS OF TREATING CANCER

(71) Applicant: Ascend Biopharmaceuticals Ltd, South Melbourne (AU)

(72) Inventor: Clement Leong, South Melbourne (AU)

(73) Assignee: Ascend Biopharmaceuticals Ltd, South Melbourne (AU)

(*) Notice: Subject to any disclaimer, the term of this patent is extended or adjusted under 35 U.S.C. 154(b) by 501 days.

(21) Appl. No.: 16/320,517

(22) PCT Filed: Jul. 24, 2017

(86) PCT No.: PCT/AU2017/050760
§ 371 (c)(1),
(2) Date: Jan. 25, 2019

(87) PCT Pub. No.: WO2018/018073
PCT Pub. Date: Feb. 1, 2018

(65) Prior Publication Data
US 2019/0269711 A1    Sep. 5, 2019

(30) Foreign Application Priority Data

Jul. 25, 2016   (AU) .................................. 2016902922
Jul. 25, 2016   (AU) .................................. 2016902923

(51) Int. Cl.
*A61K 31/706*   (2006.01)
*A61K 31/235*   (2006.01)
*A61K 31/4439*  (2006.01)
*A61K 31/505*   (2006.01)
*A61K 31/7105*  (2006.01)
*A61K 31/713*   (2006.01)
*A61K 31/739*   (2006.01)
*A61K 35/761*   (2015.01)
*A61K 38/19*    (2006.01)
*A61K 38/20*    (2006.01)
*A61K 38/21*    (2006.01)
*A61K 9/00*     (2006.01)
*A61P 35/00*    (2006.01)
*C12N 15/86*    (2006.01)
*C07K 14/57*    (2006.01)
*A61K 38/16*    (2006.01)
*A61K 31/22*    (2006.01)
(Continued)

(52) U.S. Cl.
CPC .......... *A61K 31/706* (2013.01); *A61K 9/0014* (2013.01); *A61K 31/22* (2013.01); *A61K 31/235* (2013.01); *A61K 31/4439* (2013.01); *A61K 31/505* (2013.01); *A61K 31/513* (2013.01); *A61K 31/713* (2013.01); *A61K 31/7105* (2013.01); *A61K 31/739* (2013.01); *A61K 35/761* (2013.01); *A61K 38/16* (2013.01); *A61K 38/19* (2013.01); *A61K 38/191* (2013.01); *A61K 38/195* (2013.01); *A61K 38/208* (2013.01); *A61K 38/2086* (2013.01); *A61K 38/21* (2013.01); *A61K 38/217* (2013.01); *A61K 45/06* (2013.01); *A61P 35/00* (2018.01); *C07K 14/57* (2013.01); *C12N 15/86* (2013.01); *C12N 2710/10033* (2013.01); *C12N 2710/10043* (2013.01); *C12N 2710/10333* (2013.01); *C12N 2710/10343* (2013.01); *C12N 2770/24032* (2013.01); *C12N 2770/24043* (2013.01)

(58) Field of Classification Search
None
See application file for complete search history.

(56) References Cited

U.S. PATENT DOCUMENTS

2001/0006633 A1* 7/2001 Kirn .................... A61K 45/06
424/93.6

OTHER PUBLICATIONS

Slos, et al. (2004) "Intra-tumoral delivery of TG1024 . . . or TG1042 . . . with systemic chemotherapy: Preclinical studies in murine models", Cancer Research, 64(7 Suppl.) 1063, Abstract 4605. (Year: 2004).*
Van Ruth, et al. (2006) "Total body topical 5-fluorouracil for extensive non-melanoma skin cancer", Pharm world Sci, 28: 159-62. (Year: 2006).*
Panozzo, et al. (1996) "Cytokines may influence tumor growth and spread" Int. J. Clin. Lab. Res. 26: 240-44. (Year: 1996).*

(Continued)

*Primary Examiner* — Robert M Kelly

(74) *Attorney, Agent, or Firm* — Wolf, Greenfield & Sacks, P.C.

(57) ABSTRACT

The present invention relates to methods of treating cancer in a human subject in need thereof. In particular, the present invention relates to treating a cancer by administering a recombinant virus which expresses one or more biotherapeutic agents in a subject, and administering to the subject a nucleotide analogue or nucleotide precursor analogue chemotherapeutic agent. The invention further relates to method for treating cancer by administering a nucleotide analogue or nucleotide precursor analogue chemotherapeutic agent and a caspase inhibitor, and, optionally, also administering a recombinant virus expressing one or more biotherapeutic agents in the subject. The invention also relates to a method for treating cancer by administering purified interferon gamma to a subject and administering to the subject a nucleotide analogue or nucleotide precursor analogue chemotherapeutic agent. Also provided are pharmaceutical compositions, including controlled release pharmaceutical compositions containing: a nucleotide analogue or nucleotide precursor analogue chemotherapeutic agent and a recombinant virus; a nucleotide analogue or nucleotide analogue precursor chemotherapeutic agent and a caspase inhibitor; or a purified interferon gamma and a nucleotide analogue or nucleotide precursor analogue chemotherapeutic agent.

16 Claims, 25 Drawing Sheets

(51) Int. Cl.
   *A61K 31/513* (2006.01)
   *A61K 45/06* (2006.01)

(56) References Cited

OTHER PUBLICATIONS

Seruga, et al. (2008) "Cytokines and their relationship to the symptoms and outcome of cancer", Nature Reviews Cancer, 8: 887-99.*
Gartung, et al. (2019) "Suppression of chemotherapy-induced cytokine/lipid mediator surge and ovarian cancer by a duel Cox-2sEH inhibitor", Proceedings of the National Academy of Science, USA, 116(5): 1698-1703. (Year: 2019).*
International Search Report and Written Opinion for Application No. PCT/AU2017/050760 dated Aug. 17, 2017.
International Preliminary Report on Patentability for Application No. PCT/AU2017/050760 dated Feb. 7, 2019.
Ghiringhelli et al., Enhancing the anticancer effects of 5-fluorouracil: current challenges and future perspectives. Biomed J. Mar.-Apr. 2015;38(2):111-6. doi: 10.4103/2319-4170.130923.
Hwang et al., Adenovirus-mediated interleukin-12 gene transfer combined with cytosine deaminase followed by 5-fluorocytosine treatment exerts potent antitumor activity in Renca tumor-bearing mice. BMC Cancer. May 2005; 24(5) 51.-61.
Liljenfeldt et al., Enhanced therapeutic anti-tumor immunity induced by co-administration of 5-fluorouracil and adenovirus expressing CD40 ligand. Cancer Immunol Immunother. Mar. 2014;63(3):273-82. doi: 10.1007/s00262-013-1507-6. Epub Dec. 20, 2013.
Vardouli et al., Adenovirus delivery of human CD40 ligand gene confers direct therapeutic effects on carcinomas. Cancer Gene Ther. Nov. 2009;16(11):848-60. doi: 10.1038/cgt.2009.31. Epub May 22, 2009.

* cited by examiner

Figure 6C:
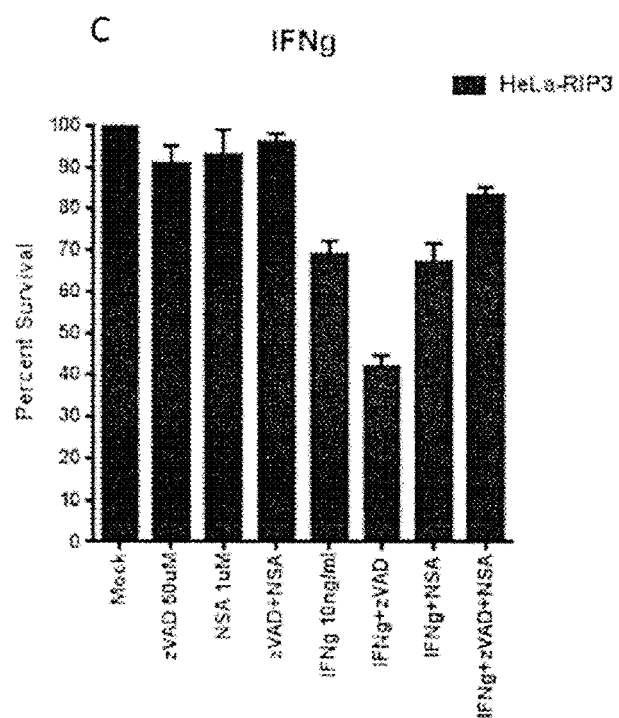

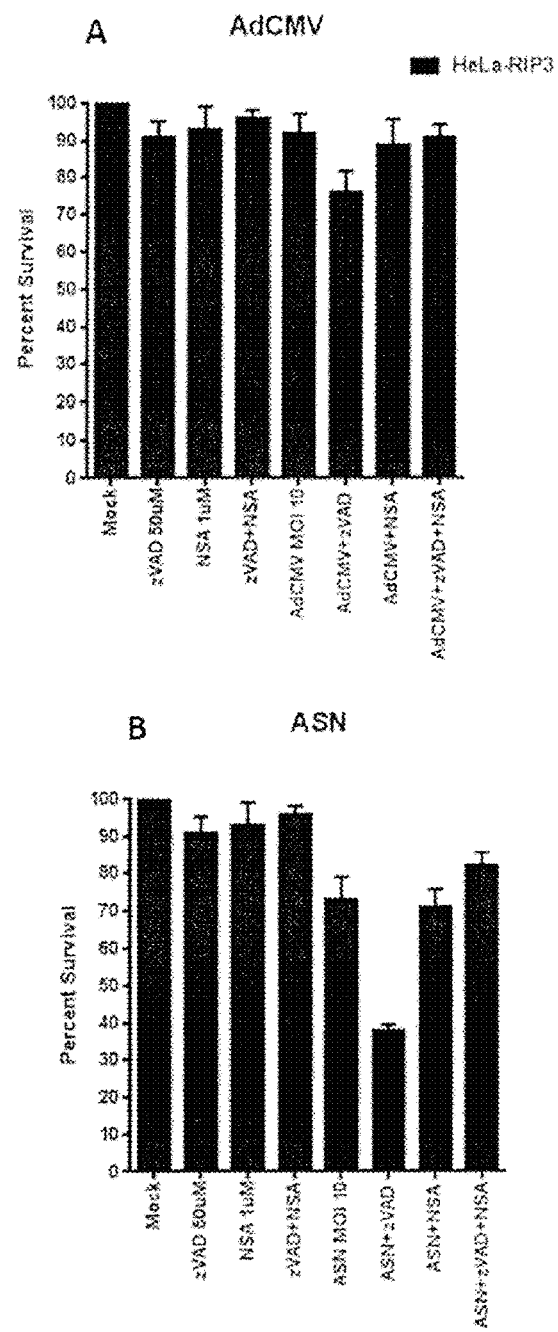
Figure 6(A-B)

Figure 8C:
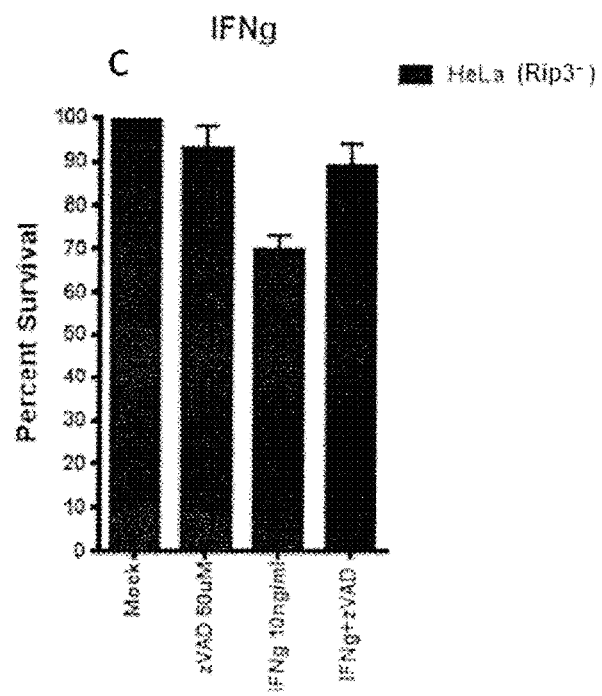

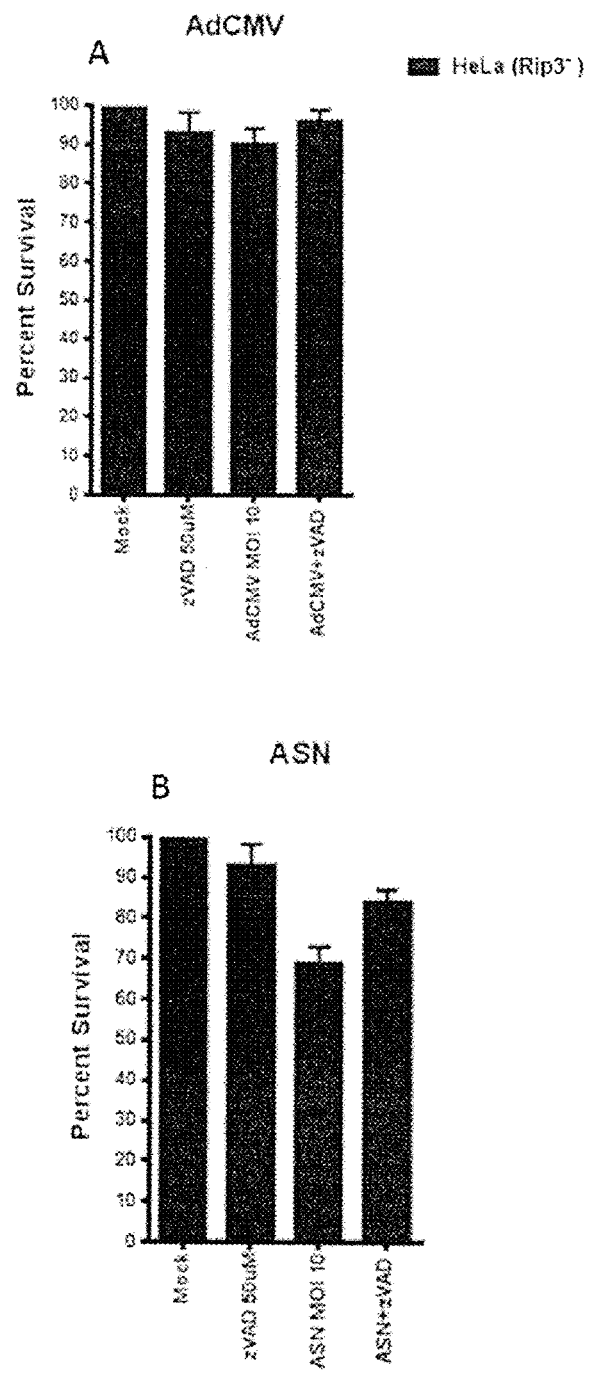
Figure 8(A-B)

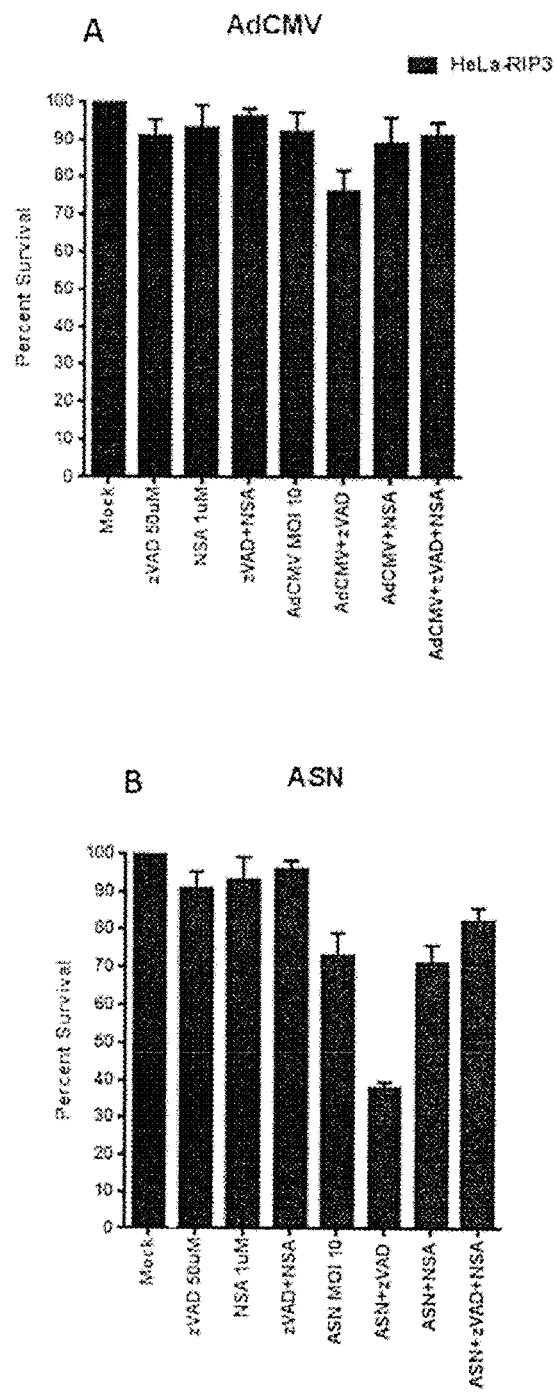
Figure 17(A-B)

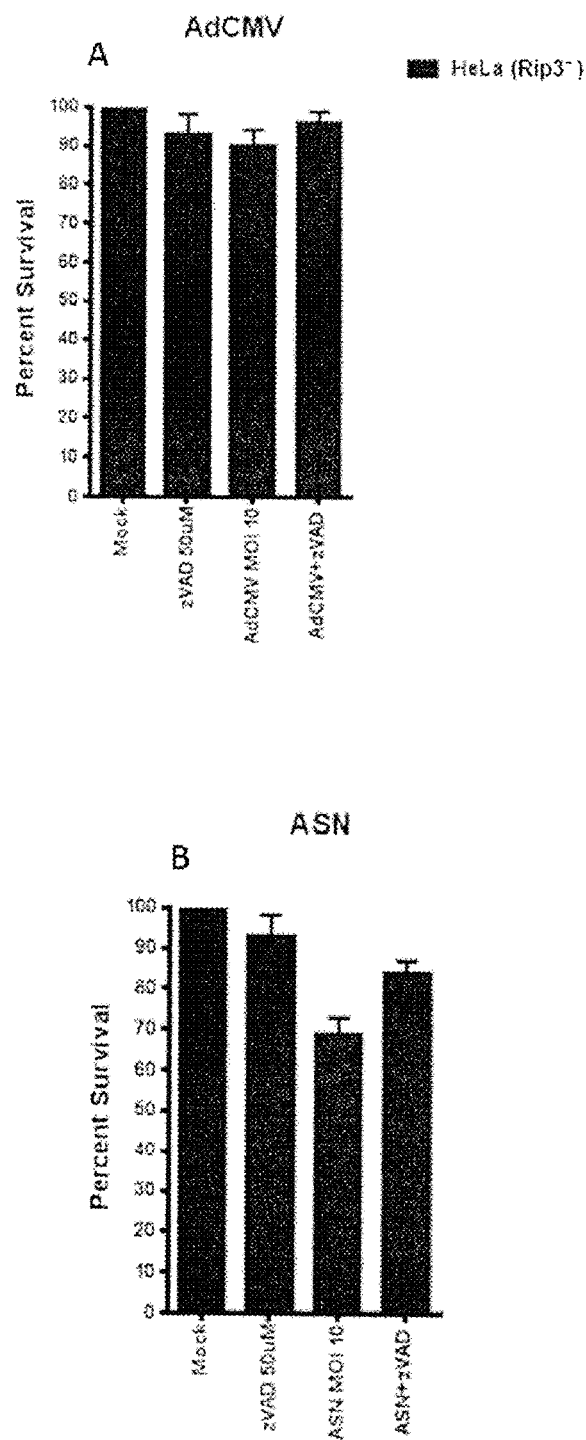
Figure 18(A-B)

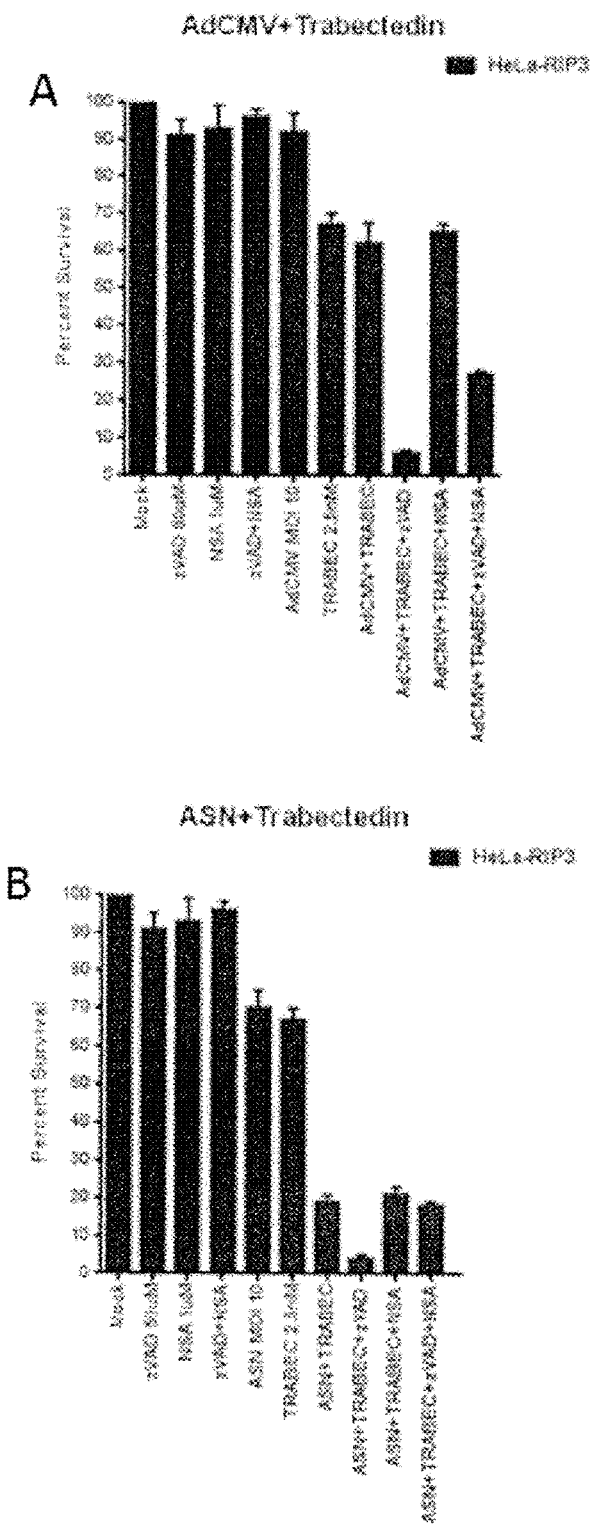
Figure 19(A-B)

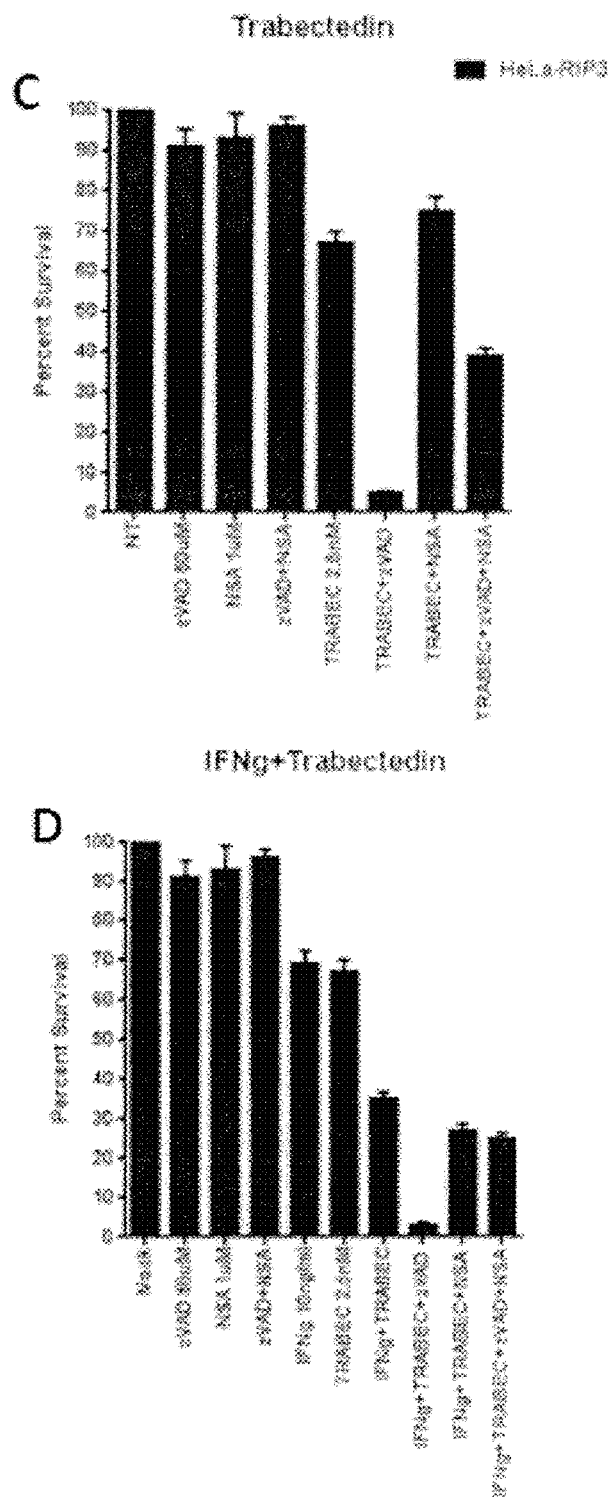
Figure 19(C-D)

METHODS OF TREATING CANCER

RELATED APPLICATIONS

This application is a national stage filing under 35 U.S.C. § 371 of international application no. PCT/AU2017/050760, filed Jul. 24, 2017, which claims the benefit of Australian Patent Application No. 2016902922 filed on Jul. 25, 2016 and the benefit of Australian Patent Application No. 2016902923 filed Jul. 25, 2016, the entire contents of each of which are herein incorporated by reference in their entirety.

FIELD OF THE INVENTION

The specification relates generally to the field of cancer therapy. More particularly, the specification relates to combination therapies for the treatment of cancer.

BACKGROUND OF THE INVENTION

The effective treatment of cancer remains an enormous challenge to clinicians. Chemotherapeutic agents, such as nucleotide analogue chemotherapeutic agents, e.g., Fluorouracil have been a mainstay of cancer chemotherapy. Nevertheless, it is very difficult to provide a dose of such agents that balances high efficacy against a cancer while avoiding severe adverse events in the patient. Further, the development of cancer resistance to chemotherapeutic agents ("chemoresistance") makes their use even more problematic. Thus, there is an ongoing need for therapeutic methods that can enhance the therapeutic index of chemotherapeutic agents and potentially reduce or neutralize the impact of chemoresistance on cancer therapy.

SUMMARY OF THE INVENTION

It was found that a combination of nucleotide analogue or nucleotide precursor analogue chemotherapeutic agents (e.g., Fluorouracil) with certain biotherapeutic agents (e.g., interferon gamma), expressed with a viral vector, induces a synergistic level of cancer cell death that likely engages multiple cell death pathways. A similar synergistic treatment effect is also observed in response to a combination treatment using the same types of chemotherapeutic agents along with purified interferon gamma.

It has also been found that, surprisingly, a combination of nucleotide analogue or nucleotide precursor analogue chemotherapeutic agents with a caspase inhibitor induces an enhanced level of cancer cell death. While not wishing to be bound by theory, it is believed that inhibition of, or a deficiency in, caspase-dependent cell death effectively results in "shunting" to other cell death pathways, particularly necroptosis, in response to treatment with nucleotide analogue or nucleotide precursor analogue chemotherapeutic agents (e.g., Fluorouracil) in the combination treatments described herein.

Accordingly in one aspect provided herein is a method of treating a human subject suffering from a cancer, where the method comprises the steps of:
(i) administering to the human subject a recombinant virus which expresses one or more biotherapeutic agents in the human subject; and
(ii) administering to the human subject a chemotherapeutic agent, wherein the chemotherapeutic agent is a nucleotide analogue or a nucleotide precursor analogue. In some embodiments, this method further includes administering a caspase inhibitor to the human subject.

In another aspect provided herein is a method of treating a human subject suffering from a cancer, where the method comprises the steps of:
(i) administering to the human subject a chemotherapeutic agent, wherein the chemotherapeutic agent is a nucleotide analogue or a nucleotide precursor analogue; and
(ii) administering to the human subject a caspase inhibitor.

In a further aspect provided herein is a method of treating a human subject suffering from a cancer, where the method the steps of:
(i) administering to the human subject purified interferon gamma; and
(ii) administering to the human subject a chemotherapeutic agent, wherein the chemotherapeutic agent is a nucleotide analogue or a nucleotide precursor analogue. In some embodiments, this method further includes administering a caspase inhibitor to the human subject.

In some preferred embodiments, where a caspase inhibitor is to be administered, the caspase inhibitor is Emricasan, Pralnacasan, VX-799, VX-765, or NCX-1000.

In some embodiments, of any of the above-mentioned methods the nucleotide analogue or nucleotide precursor analogue chemotherapeutic agent is selected from among Fluorouracil (Fluorouracil), Azacitidine, Azathioprine, Capecitabine, Cladribine, Clofarabine, Cytarabine, Decitabine, Emtricitabine, Doxifluridine, Fludarabine, Gemcitabine, Mercaptopurine, Nelarabine, and Thioguanine. In some preferred embodiments, the nucleotide analogue chemotherapeutic agent to be administered is Fluorouracil.

In some embodiments, the dose of the administered chemotherapeutic agent avoids induction of more than a moderate adverse event in the human subject. In some embodiments, the dose of the nucleotide analogue or a nucleotide precursor analogue chemotherapeutic agent, when administered systemically, is about 0.01 mg/kg to about 5 mg/kg. In other embodiments, the dose of the nucleotide analogue or a nucleotide precursor analogue chemotherapeutic agent, when provided by topical administration, is provided in a topical formulation comprising the chemotherapeutic agent at a concentration of about 0.02% (w/v) to about 2% (w/v).

In some embodiments, the dose of nucleotide analogue or a nucleotide precursor analogue chemotherapeutic agent, when provided by intralesional administration, is about 0.02 mg/lesion tissue to about 10 mg/lesion.

In some embodiments, a recombinant virus to be administered is a recombinant DNA virus. In some embodiments, the recombinant DNA virus is an adenovirus, an adeno-associated virus (AAV), a herpes simplex virus (HSV), or a lentivirus. In some preferred embodiments, the recombinant DNA virus is an adenovirus or lentivirus. In a more preferred embodiment, the recombinant DNA virus is an adenovirus. In one preferred embodiment, the recombinant adenovirus is ASN-002.

In other embodiments, a recombinant virus to be administered is a recombinant RNA virus. In some embodiments, the recombinant RNA virus is an Alphavirus, a Flavivirus, a Paramyxovirus, a Rhabdovirus, or a Orthomyxovirus. In some preferred embodiments, the Flavivirus is a Kunjin virus.

In some embodiments, where the treatment method includes administration of a recombinant virus, the recombinant virus has targeted tropism. In some embodiments, expression of the one or more biotherapeutic agents from the administered recombinant virus is driven by a target selective promoter or an inducible promoter.

In some embodiments, where the treatment method includes administration of a recombinant virus expressing one or more biotherapeutic agents, such biotherapeutic agents include one or more of a cytokine, a protein regulating apoptotic cell death, a protein regulating necroptotic cell death, a protein regulating parthanatos cell death, or a protein regulating autophagic cell death.

In some preferred embodiments, the expressed biotherapeutic agent is a cytokine. In some embodiments, the expressed cytokine is interferon gamma, interferon alpha, TNF alpha, or TRAIL. In some preferred embodiments, the expressed cytokine is interferon gamma.

In some embodiments, any of the above-mentioned treatment methods can further include administering to the human subject one or more immune response-inducing or enhancing agents. In some embodiments, the one or more immune response-inducing agents include (i) a purified polarising cytokine or a purified chemokine, and (ii) a purified pro-inflammatory agent. In some embodiment the purified polarising cytokine is selected from among IL-12, IL-15, IL-18, IL-21, IL-23, and IL-27. In some embodiments, the purified chemokine is selected from among CXCL1, CCL25, and CCL27. In some embodiments, the purified pro-inflammatory agent is Ingenol mebutate. In other embodiments, the purified pro-inflammatory agent includes a toll-like receptor (TLR) agonist. In some embodiments, the TLR agonist is selected from among Poly I:C, Poly A:U, lipopolysaccharides, Mannans, CpG, Resiquimod, Imiquimod, and Glycoinositolphospholipids.

In some embodiments, administrations performed in the treatment method are performed separately. In other embodiments, administration of the nucleotide analogue or nucleotide precursor analogue chemotherapeutic agent in a combined pharmaceutical composition comprising: (i) the chemotherapeutic agent and (ii) one or more of the recombinant virus, the caspase inhibitor, or the purified interferon gamma.

In some preferred embodiments, the subject to be treated is suffering from a cancer selected from among basal cell carcinoma, squamous cell carcinoma, colorectal cancer, ovarian cancer, breast cancer, gastric cancer, and pancreatic cancer. In some preferred embodiments the cancer to be treated is basal cell carcinoma or squamous cell carcinoma.

In some embodiments, the subject to be treated is suffering from a cancer that includes cells deficient in a caspase-dependent cell death pathway. In some embodiments, such cancer cells deficient in a caspase-dependent cell death pathway are deficient in expression or function of a caspase or FADD.

In other embodiments, the cancer includes cells that are deficient in a necroptotic cell death pathway. In some embodiments, such cancer cells deficient in a necroptotic cell death pathway are deficient in the expression or function of RIPK1, RIPK3, or MLKL.

In some embodiments of any of the above-referenced treatment methods, the human subject to be treated was identified prior to treatment as suffering from a cancer that is refractory or resistant to treatment with one or more chemotherapeutic agents alone.

In some embodiments, any of the above-mentioned methods include a step of determining prior to the first administration step a likelihood that the human subject to be treated is suffering from a cancer that is refractory or resistant to treatment with chemotherapeutic agents alone. In some embodiments, determining the likelihood that the cancer is refractory or resistant to treatment with one or more chemotherapeutic agents alone includes determining if the cancer includes cells deficient in an apoptotic cell death pathway or a necroptotic cell death pathway.

In a related aspect provided herein is the use of a recombinant virus which expresses one or more biotherapeutic agents in a human subject for the manufacture of a medicament for the treatment of a cancer in the human subject, wherein the human subject has been or will be administered a nucleotide analogue or a nucleotide precursor analogue chemotherapeutic agent.

In a further related aspect provided herein is the use of a nucleotide analogue or nucleotide precursor analogue chemotherapeutic agent for the manufacture of a medicament for the treatment of a cancer in a human subject, wherein the human subject has been or will be administered with a recombinant virus which expresses one or more biotherapeutic agents in the human subject.

In another aspect provided herein is the use of a caspase inhibitor for the manufacture of a medicament for the treatment of a cancer in a human subject, wherein the human subject has been or will be administered a nucleotide analogue or nucleotide precursor analogue chemotherapeutic agent.

In a related aspect provided herein is the use of a nucleotide analogue or nucleotide precursor analogue chemotherapeutic agent for the manufacture of a medicament for the treatment of a cancer in a human subject, wherein the human subject has been or will be administered a caspase inhibitor.

In a further aspect provided herein is the use of purified interferon gamma for the manufacture of a medicament for the treatment of a cancer in a human subject, wherein the human subject has been or will be administered a nucleotide analogue or nucleotide precursor analogue chemotherapeutic agent.

In a related aspect provided herein is the use of a nucleotide analogue or nucleotide precursor analogue chemotherapeutic agent for the manufacture of a medicament for the treatment of a cancer in a human subject, wherein the human subject has been or will be administered purified interferon gamma.

In an additional aspect provided herein is a recombinant virus which expresses one or more biotherapeutic agents in a human subject for use in a method of treating a cancer in a human subject, wherein the human subject has been or will be administered a nucleotide analogue or a nucleotide precursor analogue chemotherapeutic agent.

In a related aspect provided herein is nucleotide analogue or nucleotide precursor analogue chemotherapeutic agent for use in a method of treating a cancer in a human subject, wherein the human subject has been or will be administered a recombinant virus which expresses one or more biotherapeutic agents in a human subject.

In a further aspect provided herein is a caspase inhibitor for use in a method of treating a cancer in a human subject, wherein the human subject has been or will be administered a nucleotide analogue or a nucleotide precursor analogue chemotherapeutic agent.

In a related aspect provided herein is a nucleotide analogue or nucleotide precursor analogue chemotherapeutic agent for use in a method of treating a cancer in a human subject, wherein the human subject has been or will be administered a caspase inhibitor.

In another aspect provided herein is purified interferon gamma for use in a method of treating a cancer in a human subject, wherein the human subject has been or will be administered a nucleotide analogue or a nucleotide precursor analogue chemotherapeutic agent.

In a related aspect provided herein is a nucleotide analogue or a nucleotide precursor analogue chemotherapeutic agent for use in a method of treating a cancer in a human subject, wherein the human subject has been or will be administered interferon gamma.

In yet another aspect provided herein is a pharmaceutical composition for use in the treatment of a cancer, the pharmaceutical composition comprising:

(i) a recombinant expression virus for expression of one or more biotherapeutic agents in a human subject; and (ii) a nucleotide analogue or a nucleotide precursor analogue chemotherapeutic agent.

In a further aspect provided herein is a pharmaceutical composition for use in the treatment of a cancer, the pharmaceutical composition comprising:

(i) a caspase inhibitor; and (ii) a nucleotide analogue or a nucleotide precursor analogue chemotherapeutic agent.

In another aspect provided herein is a pharmaceutical composition for use in the treatment of a cancer, the pharmaceutical composition comprising:

(i) purified interferon gamma; and (ii) a nucleotide analogue or a nucleotide precursor analogue chemotherapeutic agent.

In preferred embodiments of the above-mentioned pharmaceutical compositions, the dose of the nucleotide analogue or nucleotide precursor analogue chemotherapeutic agent provided in the pharmaceutical composition avoids induction of more than a moderate adverse event in the human subject. In some preferred embodiments the cancer to be treated is selected from the group consisting of basal cell carcinoma, squamous cell carcinoma, colorectal cancer, ovarian cancer, breast cancer, gastric cancer, and pancreatic cancer. In some preferred embodiments the cancer to be treated is basal cell carcinoma or squamous cell carcinoma.

In some embodiments, the above-mentioned pharmaceutical compositions also include a controlled release matrix. In some embodiments, the controlled release matrix comprises a $SiO_2$ matrix gel.

In some preferred embodiments, the nucleotide analogue chemotherapeutic agent is Fluorouracil.

It was also found that a combination of chemotherapeutic agents other than nucleotide analogue or nucleotide precursor analogue chemotherapeutic agents (e.g., Trabectedin) with certain biotherapeutic agents (e.g., purified interferon gamma), expressed with a viral vector, induces a synergistic level of cancer cell death that likely engages multiple cell death pathways. A similar synergistic treatment effect is also observed in response to a combination treatment using the same types of chemotherapeutic agents along with purified interferon gamma.

It has also been found that, surprisingly, a combination of non-nucleotide analogue chemotherapeutic agents with a caspase inhibitor induces an enhanced level of cancer cell death. While not wishing to be bound by theory, it is believed that inhibition of, or a deficiency in, caspase-dependent cell death effectively results in "shunting" to other cell death pathways, particularly necroptosis, in response to treatment with chemotherapeutic agents (e.g., Trabectedin) in the combination treatments described herein.

In another aspect provided herein is a method of treating a human subject suffering from a cancer, where the method comprises the steps of:

(i) administering to the human subject a recombinant virus which expresses one or more biotherapeutic agents in the human subject; and (ii) administering to the human subject a chemotherapeutic agent other than a nucleotide analogue or a nucleotide precursor analogue. In some embodiments, this method further includes administering a caspase inhibitor to the human subject.

In another aspect provided herein is a method of treating a human subject suffering from a cancer, where the method comprises the steps of:

(i) administering to the human subject a chemotherapeutic agent other than a nucleotide analogue or a nucleotide precursor analogue; and (ii) administering to the human subject a caspase inhibitor.

In a further aspect provided herein is a method of treating a human subject suffering from a cancer, where the method the steps of:

(i) administering to the human subject purified interferon gamma; and (ii) administering to the human subject a chemotherapeutic agent other than a nucleotide analogue or a nucleotide precursor analogue. In some embodiments this method further includes administering a caspase inhibitor to the human subject.

In some preferred embodiments, where a caspase is to be administered, the caspase inhibitor is Emricasan, Pralnacasan, VX-799, VX-765, or NCX-1000.

In some embodiments of any of the above-mentioned methods the chemotherapeutic agent is of a class selected from among DNA-binding agents, second mitochondrial-derived activator of caspases (SMAC) mimetics, alkylating agents, topoisomerase inhibitors, nucleoside analogs, proteasome inhibitors, and poly ADP ribose polymerase (PARP) inhibitors. In some preferred embodiments of any of the above-mentioned methods the chemotherapeutic agent is Trabectedin or Biranapant. In other preferred embodiments the chemotherapeutic agent is Trabectedin.

In some embodiments the dose of the administered chemotherapeutic agent avoids induction of more than a moderate adverse event in the human subject.

In some embodiments, a recombinant virus to be administered is a recombinant DNA virus. In some embodiments, the recombinant DNA virus is an adenovirus, an adeno-associated virus (AAV), a herpes simplex virus (HSV), or a lentivirus. In some preferred embodiments, the recombinant DNA virus is an adenovirus or lentivirus.

In other embodiments, a recombinant virus to be administered is a recombinant RNA virus. In some embodiments, the recombinant RNA virus is an Alphavirus, a Flavivirus, a Paramyxovirus, a Rhabdovirus, or a Orthomyxovirus. In some preferred embodiments, the Flavivirus is a Kunjin virus.

In some embodiments, where the treatment method includes administration of a recombinant virus, the recombinant virus has targeted tropism. In some embodiments, expression of the one or more biotherapeutic agents from the administered recombinant virus is driven by a target selective promoter or an inducible promoter.

In some embodiments, where the treatment method includes administration of a recombinant virus expressing one or more biotherapeutic agents, such biotherapeutic agents include one or more of a cytokine, a protein regulating apoptotic cell death, a protein regulating necroptotic cell death, a protein regulating parthanatos cell death, or a protein regulating autophagic cell death.

In some embodiments, the expressed cytokine is interferon gamma, interferon alpha, TNF alpha, or TRAIL. In some preferred embodiments, the expressed cytokine is interferon gamma.

In some embodiments, any of the above-mentioned treatment methods can further include administering to the human subject one or more immune response-inducing or enhancing agents. In some embodiments, the one or more immune response-inducing agents include (i) a purified polarising cytokine or a purified chemokine, and (ii) a purified pro-inflammatory agent. In some embodiment the purified polarising cytokine is selected from among IL-12, IL 15, IL-18, IL-21, IL-23, and IL-27. In some embodiments, the purified chemokine is selected from among CXCL1, CCL25, and CCL27. In some embodiments, the purified pro-inflammatory agent is Ingenol mebutate. In other embodiments, the purified pro-inflammatory agent includes a toll-like receptor (TLR) agonist. In some embodiments, the TLR agonist is selected from among Poly I:C, Poly A:U, lipopolysaccharides, Mannans, CpG, Resiquimod, Imiquimod, and Glycoinositolphospholipids.

In some embodiments administrations performed in the treatment method are performed separately. In other embodiments administration of the chemotherapeutic agent in a combined pharmaceutical composition comprising: (i) the chemotherapeutic agent and (ii) one or more of the recombinant virus, the caspase inhibitor, or the purified interferon gamma.

In some preferred embodiments, the subject to be treated is suffering from a cancer selected from among basal cell carcinoma, squamous cell carcinoma, colorectal cancer, ovarian cancer, breast cancer, gastric cancer, and pancreatic cancer.

In some embodiments, the subject to be treated is suffering from a cancer that includes cells deficient in a caspase-dependent cell death pathway. In some embodiments, such cancer cells deficient in a caspase-dependent cell death pathway are deficient in expression or function of a caspase or FADD.

In other embodiments, the cancer includes cells that are deficient in a necroptotic cell death pathway. In some embodiments, such cancer cells deficient in a necroptotic cell death pathway are deficient in the expression or function of RIPK1, RIPK3, or MLKL.

In some embodiments of any of the above-referenced treatment methods, the human subject to be treated was identified prior to treatment as suffering from a cancer that is refractory or resistant to treatment with one or more chemotherapeutic agents alone.

In some embodiments, any of the above-mentioned methods include a step of determining prior to the first administration step a likelihood that the human subject to be treated is suffering from a cancer that is refractory or resistant to treatment with chemotherapeutic agents alone. In some embodiments, determining the likelihood that the cancer is refractory or resistant to treatment with one or more chemotherapeutic agents alone includes determining if the cancer includes cells deficient in an apoptotic cell death pathway or a necroptotic cell death pathway.

In a related aspect provided herein is the use of a recombinant virus which expresses one or more biotherapeutic agents in a human subject for the manufacture of a medicament for the treatment of a cancer in the human subject, wherein the human subject has been or will be administered a chemotherapeutic agent other than a nucleotide analogue or a nucleotide precursor analogue.

In a further related aspect provided herein is the use of a chemotherapeutic agent other than a nucleotide analogue or a nucleotide precursor analogue for the manufacture of a medicament for the treatment of a cancer in a human subject, wherein the human subject has been or will be administered with a recombinant virus which expresses one or more biotherapeutic agents in the human subject.

In another aspect provided herein is the use of a caspase inhibitor for the manufacture of a medicament for the treatment of a cancer in a human subject, wherein the human subject has been or will be administered a chemotherapeutic agent other than a nucleotide analogue or a nucleotide precursor analogue.

In a related aspect provided herein is the use of a chemotherapeutic agent other than a nucleotide analogue or a nucleotide precursor analogue for the manufacture of a medicament for the treatment of a cancer in a human subject, wherein the human subject has been or will be administered a caspase inhibitor.

In a further aspect provided herein is the use of purified interferon gamma for the manufacture of a medicament for the treatment of a cancer in a human subject, wherein the human subject has been or will be administered a chemotherapeutic agent other than a nucleotide analogue or a nucleotide precursor analogue.

In a related aspect provided herein is the use of a chemotherapeutic agent other than a nucleotide analogue or a nucleotide precursor analogue for the manufacture of a medicament for the treatment of a cancer in a human subject, wherein the human subject has been or will be administered purified interferon gamma.

In an additional aspect provided herein is a recombinant virus which expresses one or more biotherapeutic agents in a human subject for use in a method of treating a cancer in the human subject, wherein the human subject has been or will be administered a chemotherapeutic agent other than a nucleotide analogue or a nucleotide precursor analogue.

In a related aspect provided herein is a chemotherapeutic agent other than a nucleotide analogue or a nucleotide precursor analogue for use in a method of treating a cancer in the human subject, wherein the human subject has been or will be administered a recombinant virus which expresses one or more biotherapeutic agents in a human subject.

In a further aspect provided herein is a caspase inhibitor for use in a method of treating a cancer in the human subject, wherein the human subject has been or will be administered a chemotherapeutic agent other than a nucleotide analogue or a nucleotide precursor analogue.

In a related aspect provided herein is a chemotherapeutic agent other than a nucleotide analogue or a nucleotide precursor analogue for use in a method of treating a cancer in the human subject, wherein the human subject has been or will be administered a caspase inhibitor.

In another aspect provided herein is purified interferon gamma for use in a method of treating a cancer in a human subject, wherein the human subject has been or will be administered a chemotherapeutic agent other than a nucleotide analogue or a nucleotide precursor analogue.

In a related aspect provided herein is a chemotherapeutic agent other than a nucleotide analogue or a nucleotide precursor analogue for use in a method of treating a cancer in a human subject, wherein the human subject has been or will be administered purified interferon gamma.

In yet another aspect provided herein is a pharmaceutical composition for use in the treatment of a cancer, the pharmaceutical composition comprising:

(i) a recombinant expression virus for expression of one or more biotherapeutic agents in a human subject; and (ii) a chemotherapeutic agent other than a nucleotide analogue or nucleotide precursor analogue chemotherapeutic agent. In some embodiments the one or more expressed biotherapeutic agents comprises a cytokine. In some embodiments the expressed cytokine is interferon gamma, interferon alpha, TNF alpha, or TRAIL. In some preferred embodiments the expressed cytokine is interferon gamma. In some preferred embodiments the non-nucleotide analogue chemotherapeutic agent in the pharmaceutical composition is Trabectedin or Birinapant. In other preferred embodiments the chemotherapeutic agent in the pharmaceutical composition is Trabectedin.

In a further aspect provided herein is a pharmaceutical composition for use in the treatment of a cancer, the pharmaceutical composition comprising:

(i) a caspase inhibitor; and (ii) a chemotherapeutic agent other than a nucleotide analogue or a nucleotide precursor analogue.

In another aspect provided herein is a pharmaceutical composition for use in the treatment of a cancer, the pharmaceutical composition comprising:

(i) purified interferon gamma; and (ii) a chemotherapeutic agent other than a nucleotide analogue or a nucleotide precursor analogue.

In preferred embodiments of any of the above-mentioned pharmaceutical compositions the dose of the chemotherapeutic agent provided in the pharmaceutical composition avoids induction of more than a moderate adverse event in the human subject.

In some embodiments the above-mentioned pharmaceutical compositions also include a controlled release matrix. In some embodiments the controlled release matrix comprises a $SiO_2$ matrix gel.

The steps, features, integers, compositions and/or therapeutic agents disclosed herein or indicated in the specification of this application individually or collectively, and any combinations of two or more of said steps or features.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (e.g. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

Figure 1:
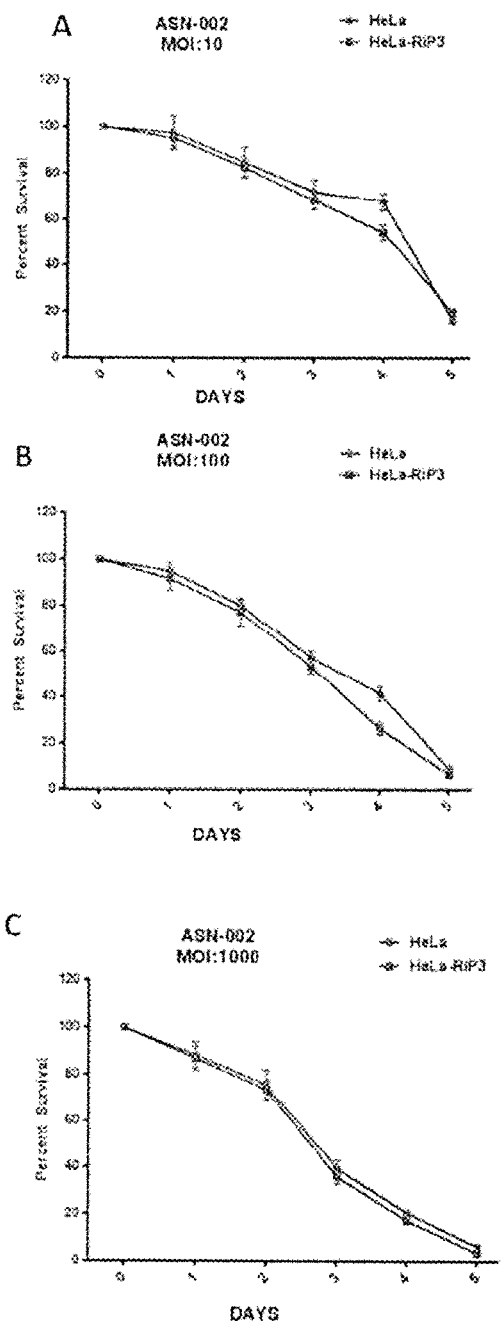

FIG. 1—ASN-002 titration of viral dose for inducing cell death in HeLa RIP3$^+$ and HeLa RIP$^-$ cells. Line graphs showing five day time course of cell death induced in cultured HeLa (RIP3$^-$) and "HeLa-RIP3" (RIP3$^+$) cells transduced with a replication-deficient recombinant adenovirus (ASN-002) expressing interferon gamma (IFN gamma) at three different multiplicities of infection (MOI). (A) MOI:10; (B) MOI:100; and (C) MOI:1000.

Figure 2:
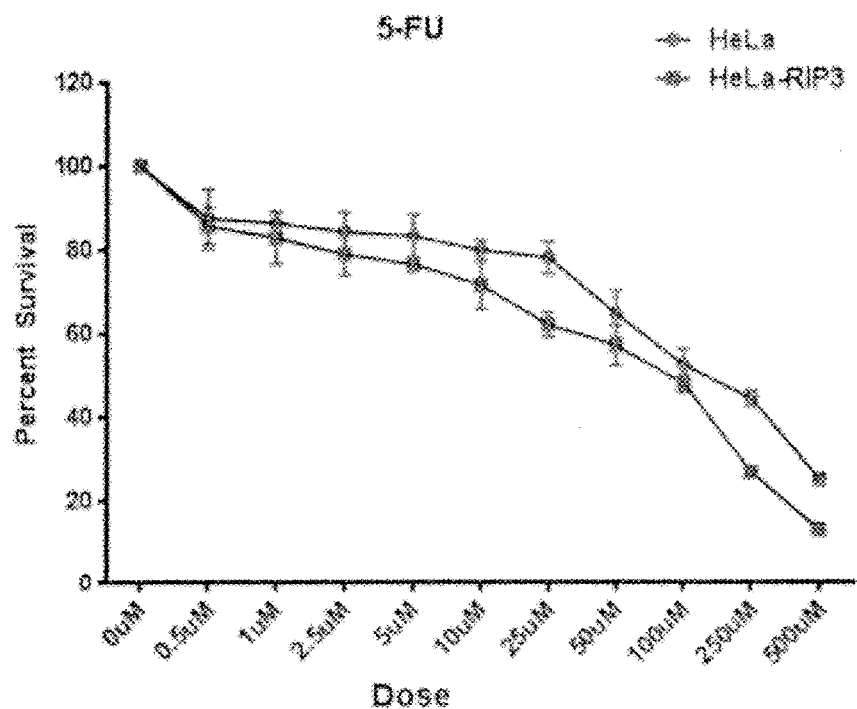

FIG. 2—Fluorouracil dose-response for inducing cell death in HeLa RIP3$^+$ and HeLa RIP$^-$ cells. Line graph showing dose-response for chemotherapeutic agent Fluorouracil-induced cell death in cultured "HeLa" (RIP3$^-$) and "HeLa-RIP3" (RIP3$^+$) cells following 48 hour exposure to Fluorouracil in culture.

Figure 3:
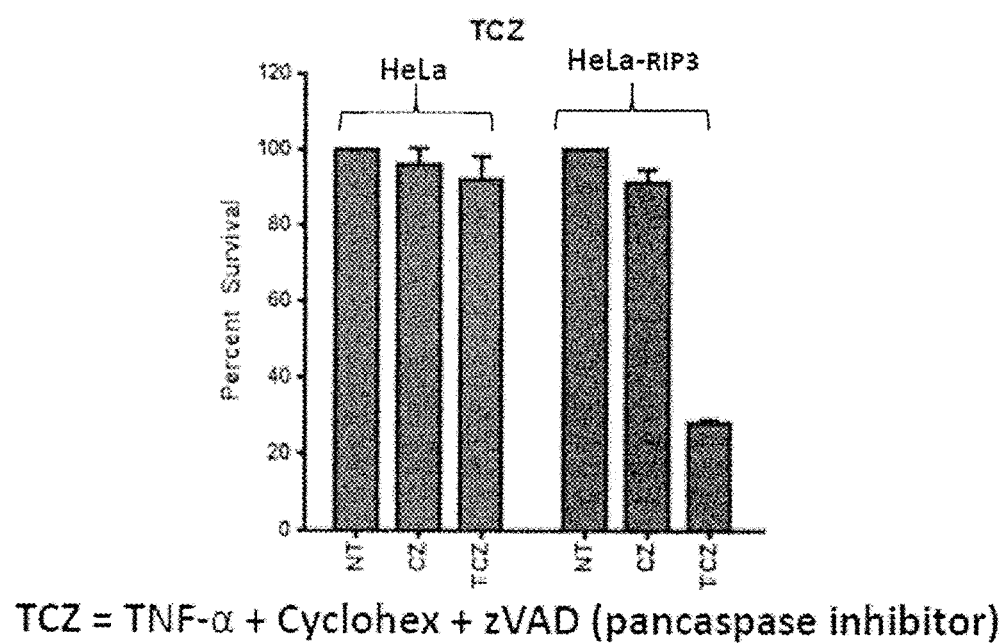

FIG. 3—The cytokine TNF alpha induces apoptosis-independent cell death in RIP3$^+$, but not RIP3$^-$ HeLa cells. Bar graphs illustrating induction of cell death by TNF alpha in cultured "HeLa-RIP3" (RIP3$^+$), necroptosis-competent HeLa cells in the presence of apoptotic cell death inhibitors, but "HeLa" (RIP3$^-$), but not in "HeLa" (RIP3$^-$), necroptosis-incompetent HeLa cells in the presence of the same apoptotic inhibitors.

Figure 4:
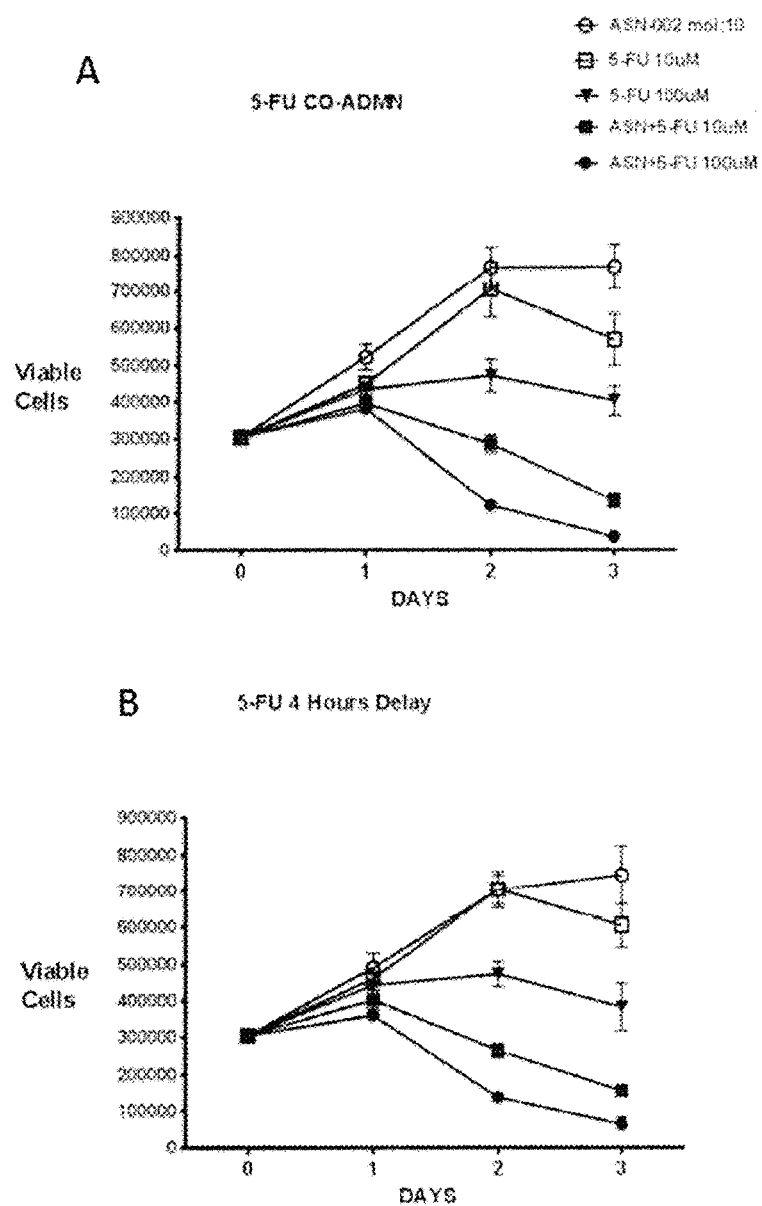

FIG. 4—Treatment of RIP3$^-$ HeLa cells with a low dose of Fluorouracil plus a low MOI of a replication-deficient recombinant adenovirus (ASN-002) expressing interferon gamma induces synergistic cell death. Line graphs illustrating cell death induced by Fluorouracil alone, ASN-002 alone, or combined treatment of Fluorouracil plus ASN-002 in cultured RIP3$^-$ HeLa cells following a 48 hour exposure. (A) Fluorouracil and ASN-002 added simultaneously to cells. (B) Fluorouracil added to cells four hours after transduction with ASN-002. Combined treatment results in significantly greater cell death than cell death resulting from either treatment alone, or the expected cell death based on the sum of cell death resulting from the individual treatments.

Figure 5:
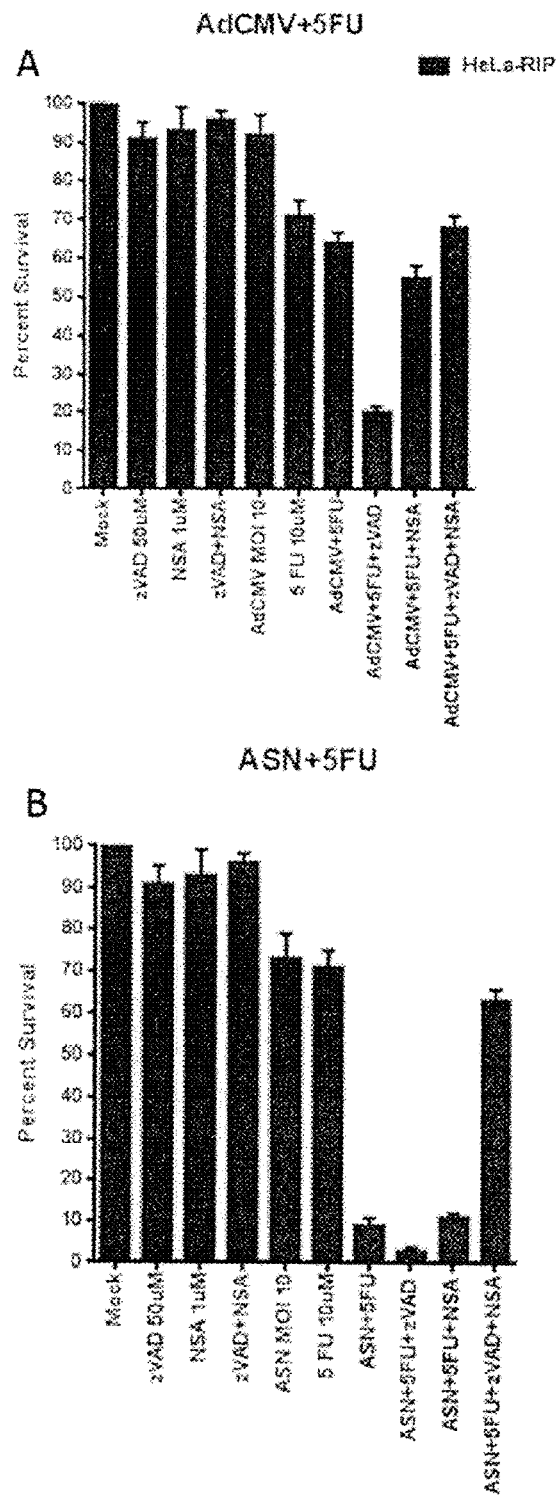

FIG. 5—Fluorouracil plus AdCMV (control), and Fluorouracil plus ASN-002 combination treatments in RIP3$^+$ HeLa cells in the presence of inhibitors of apoptosis and necroptosis. Bar graphs illustrating cell death induced in RIP3$^+$ (necroptosis-competent) HeLa cells in the presence of inhibitors of apoptosis and necroptosis by (A) Fluorouracil plus AdCMV control adenovirus; and (B) Fluorouracil plus ASN-002 adenovirus expressing IFN gamma.

FIG. 6—ASN-002 adenoviral vector-expressed IFN gamma or exogenous IFN gamma treatments in RIP3$^+$ HeLa cells in the presence of inhibitors of apoptosis and necroptosis. Bar graphs illustrating cell death induced in RIP3$^+$ (necroptosis-competent) HeLa cells in the presence of inhibitors of apoptosis and necroptosis by (A) AdCMV control adenovirus; (B) ASN-002 adenovirus expressing IFN gamma; and (C) purified IFN gamma.

Figure 7:
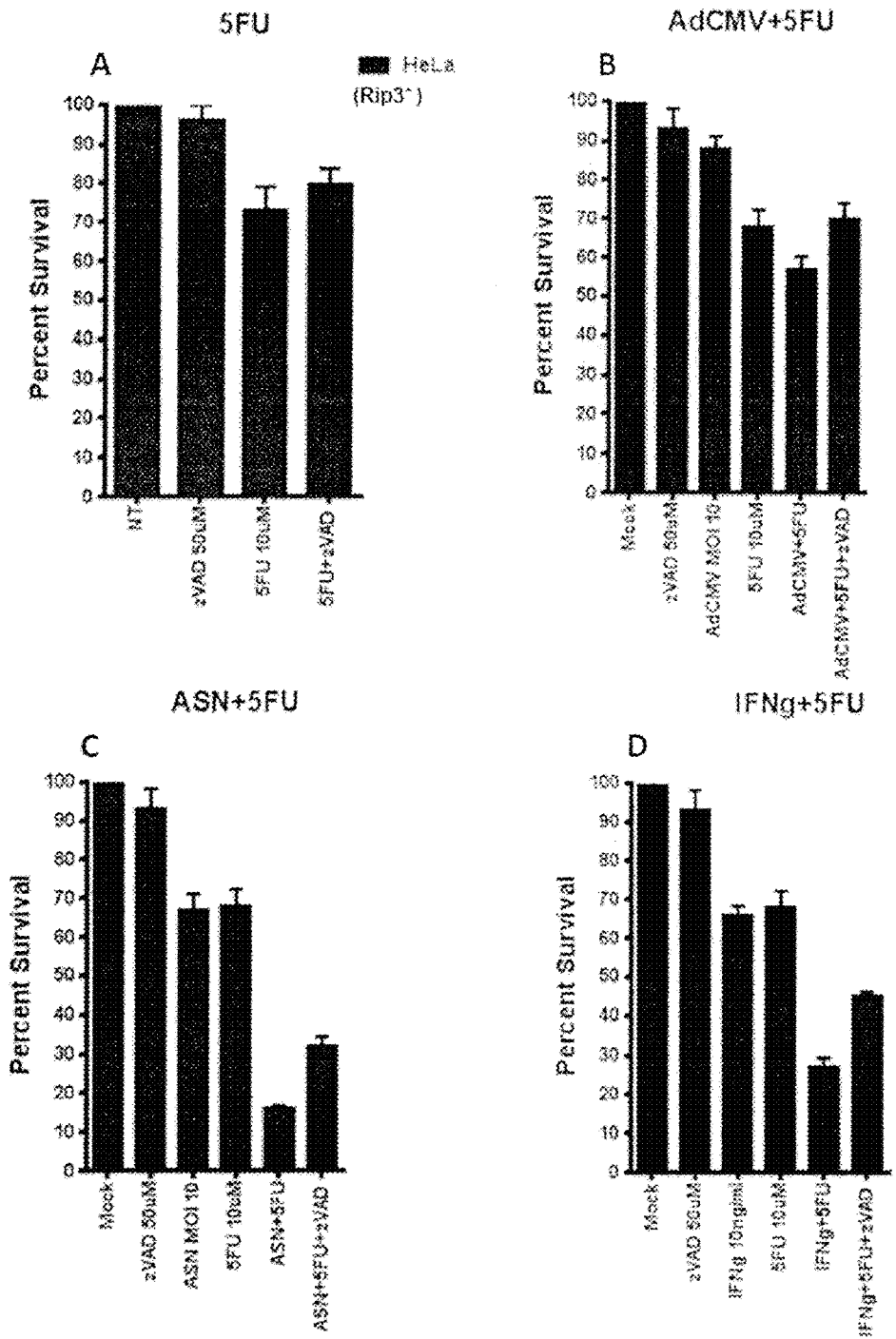

FIG. 7—Fluorouracil plus ASN-002 or purified IFN gamma combination treatments in RIP3$^-$ (necroptosis-deficient) HeLa cells in the presence of an inhibitor of apoptosis Bar graphs illustrating cell death induced in RIP3$^-$ (necroptosis-deficient) HeLa cells in the presence of a pan caspase inhibitor of apoptosis by (A) Fluorouracil alone; (B) Fluorouracil plus AdCMV control adenovirus; (C) Fluorouracil plus ASN-002 adenovirus expressing IFN gamma; and (D) Fluorouracil plus purified IFN gamma.

FIG. 8—ASN-002 adenoviral vector-expressed IFN gamma or purified IFN gamma treatments in RIP3$^-$ HeLa cells in the presence of an inhibitor of apoptosis. Bar graphs illustrating cell death induced in RIP3$^-$ (necroptosis-deficient) HeLa cells in the presence of a pan caspase inhibitor of apoptosis by (A) AdCMV control adenovirus; (B) ASN-002 adenovirus expressing IFN gamma; and (C) purified IFN gamma.

Figure 9:
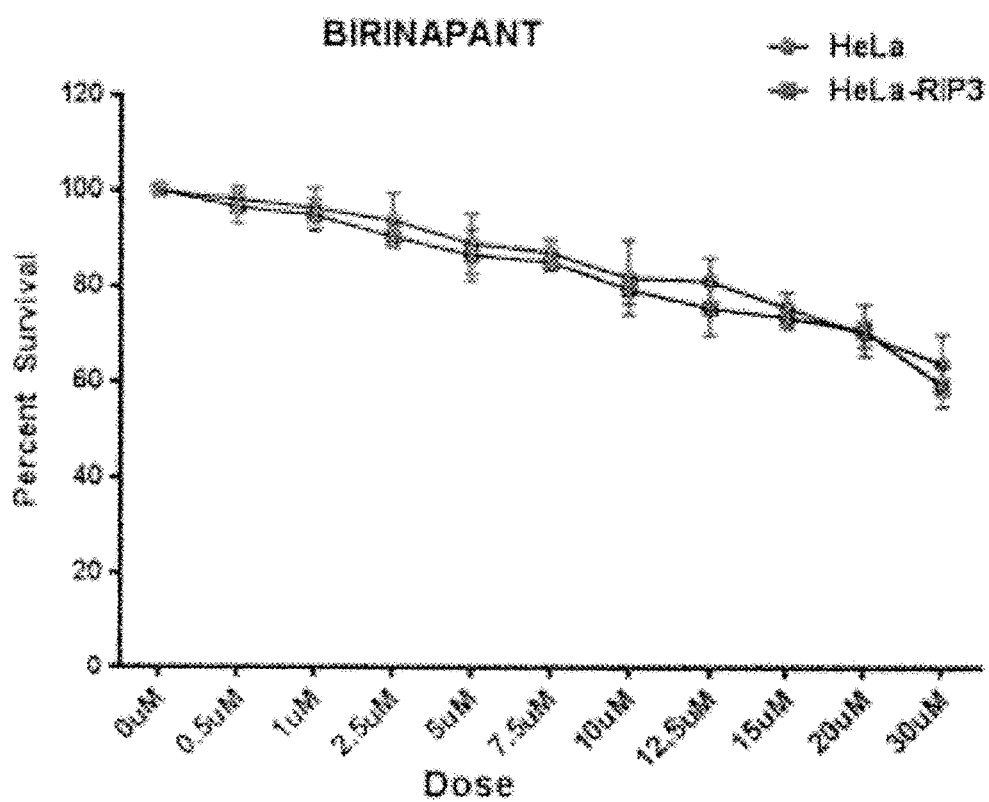

FIG. 9—Birinapant dose-response for inducing cell death in HeLa RIP3$^+$ and HeLa RIP$^-$ cells. Line graph showing dose-response for chemotherapeutic agent Birinapant-induced cell death in cultured "HeLa" (RIP3$^-$) and "HeLa- RIP3" (RIP3⁺) cells following a 48 hour exposure at the indicated concentrations in culture.

Figure 10:
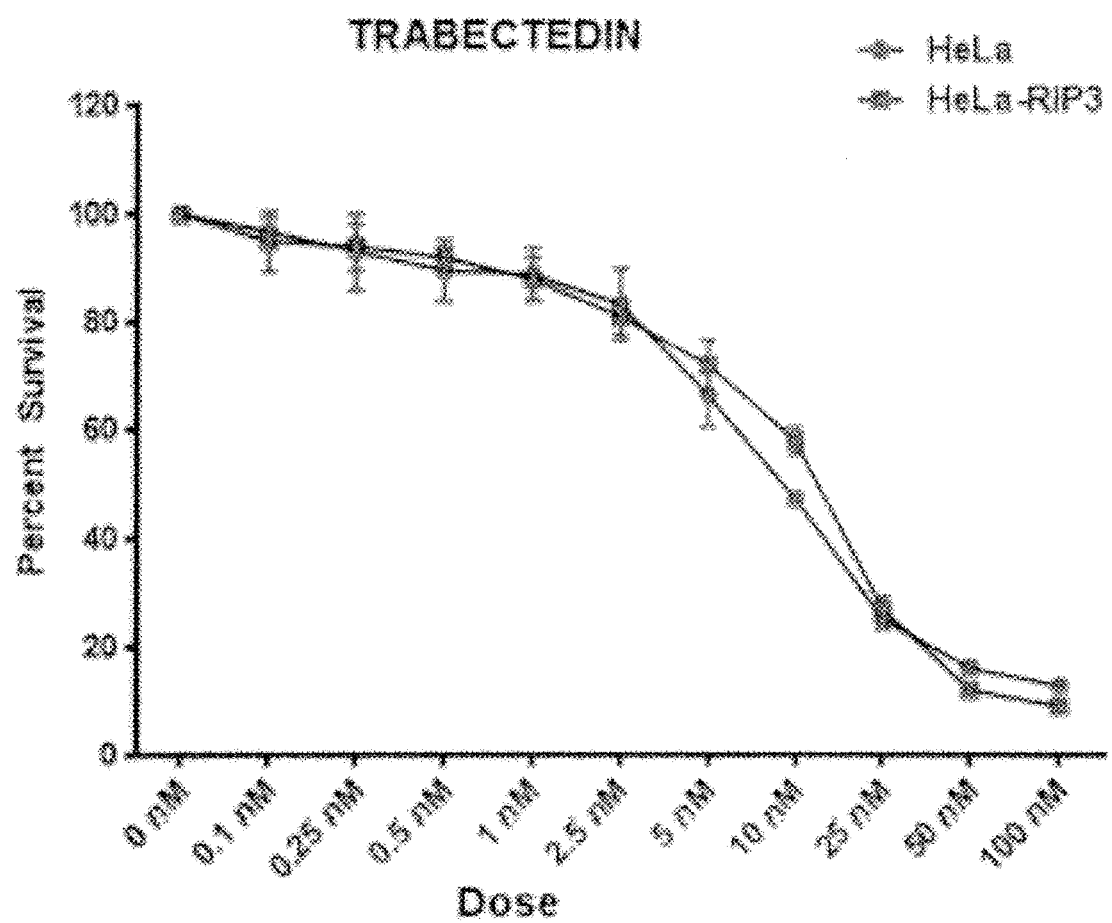

FIG. 10—Trabectedin dose-response for inducing cell death in HeLa RIP3⁺ and HeLa RIP⁻ cells. Line graph showing dose-response for chemotherapeutic agent Trabectedin-induced cell death in cultured "HeLa" (RIP3⁻) and "HeLa-RIP3" (RIP3⁺) cells following a 48 hour exposure at the indicated concentrations in culture.

Figure 11:
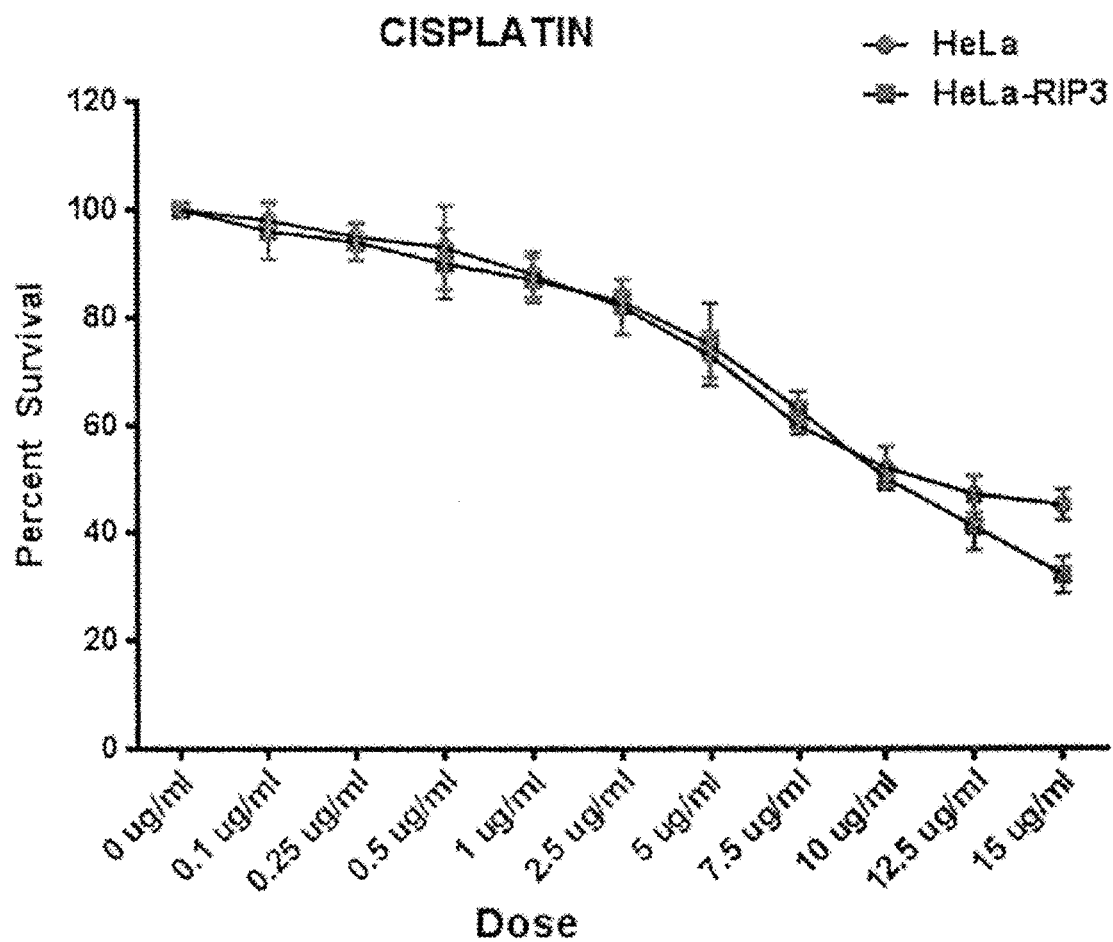

FIG. 11—Cisplatin dose-response for inducing cell death in HeLa RIP3⁺ and HeLa RIP⁻ cells. Line graph showing dose-response for chemotherapeutic agent Cisplatin-induced cell death in cultured "HeLa" (RIP3⁻) and "HeLa-RIP3" (RIP3⁺) cells following a 48 hour exposure at the indicated concentrations in culture.

Figure 12:
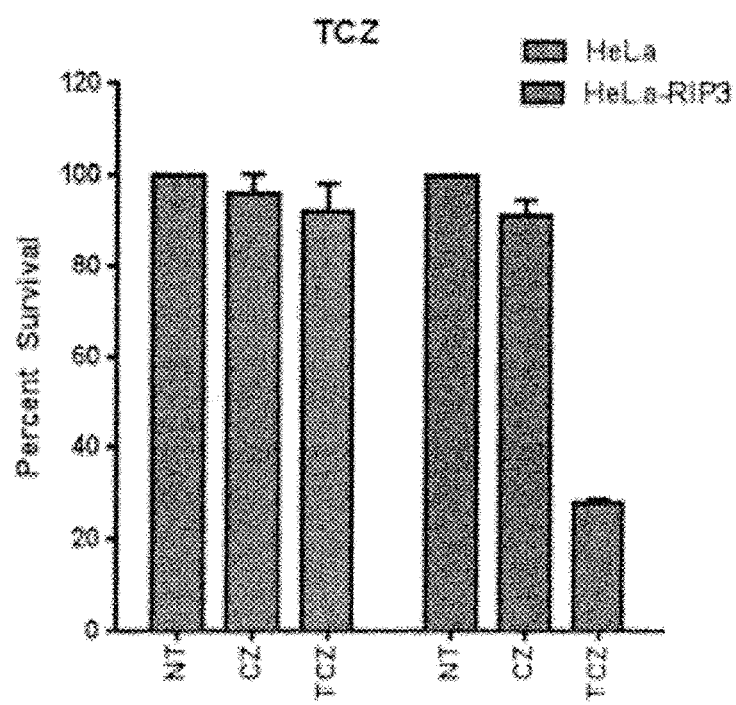

FIG. 12—The cytokine TNF alpha induces apoptosis-independent cell death in RIP3⁺, but not RIP3⁻ HeLa cells. Bar graphs illustrating induction of cell death by TNF alpha in cultured "HeLa-RIP3" (RIP3⁺), necroptosis-competent HeLa cells in the presence of apoptotic cell death inhibitors, but "HeLa" (RIP3⁻), but not in "HeLa" (RIP3⁻), necroptosis-incompetent HeLa cells in the presence of the same apoptotic inhibitors.

Figure 13:
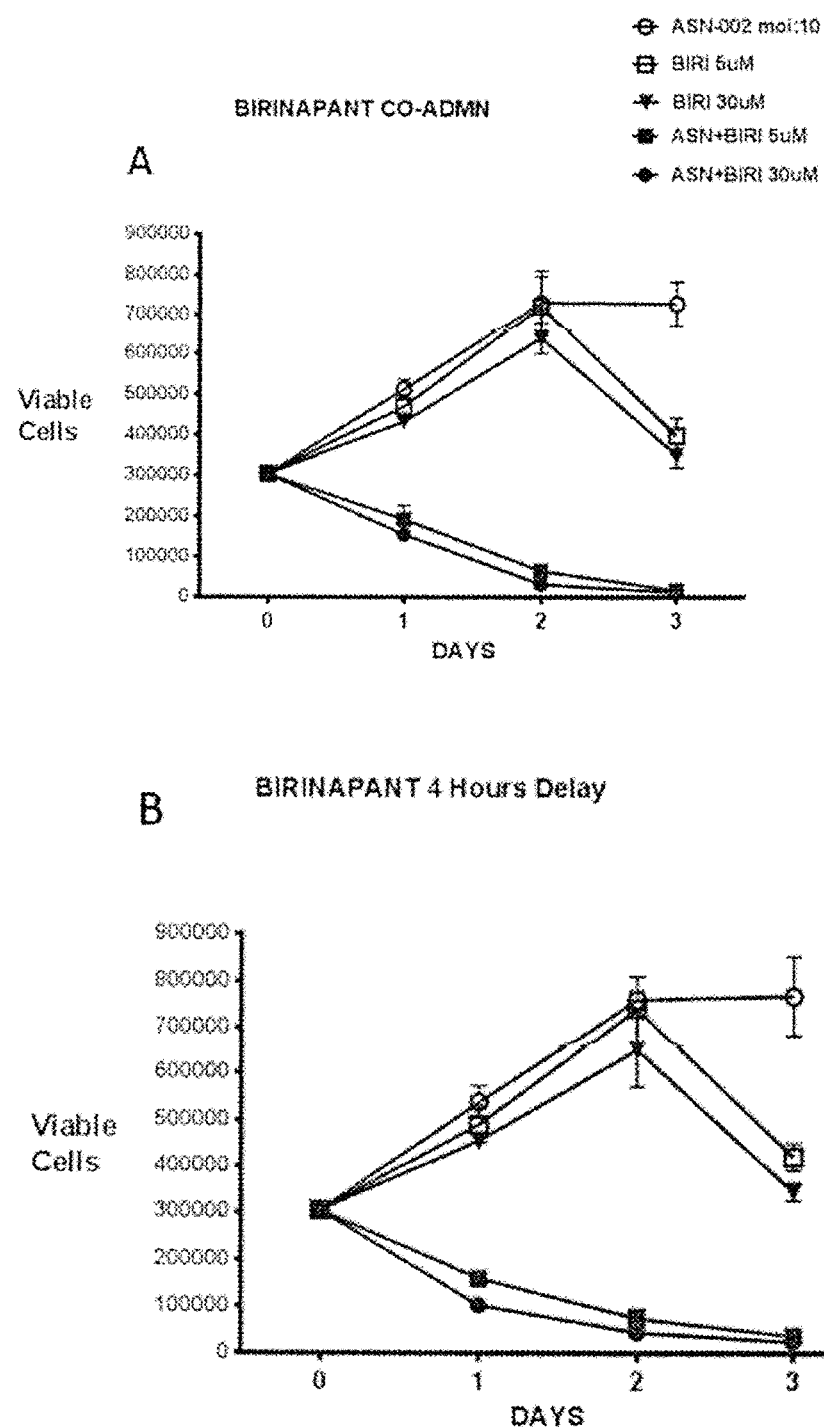

FIG. 13—Treatment of RIP3⁻ HeLa cells with a low dose of Birinapant plus a low MOI of a replication-deficient recombinant adenovirus (ASN-002) expressing interferon gamma induces synergistic cell death. Line graphs illustrating cell death induced by Birinapant alone, ASN-002 alone, or combined treatment of Birinapant plus ASN-002 in cultured RIP3⁻ HeLa cells following a 48 hour exposure. (A) Birinapant and ASN-002 added simultaneously to cells. (B) Birinapant added to cells four hours after transduction with ASN-002. Combined treatment results in significantly greater cell death than cell death resulting from either treatment alone, or the expected cell death based on the sum of cell death resulting from the individual treatments.

Figure 14:
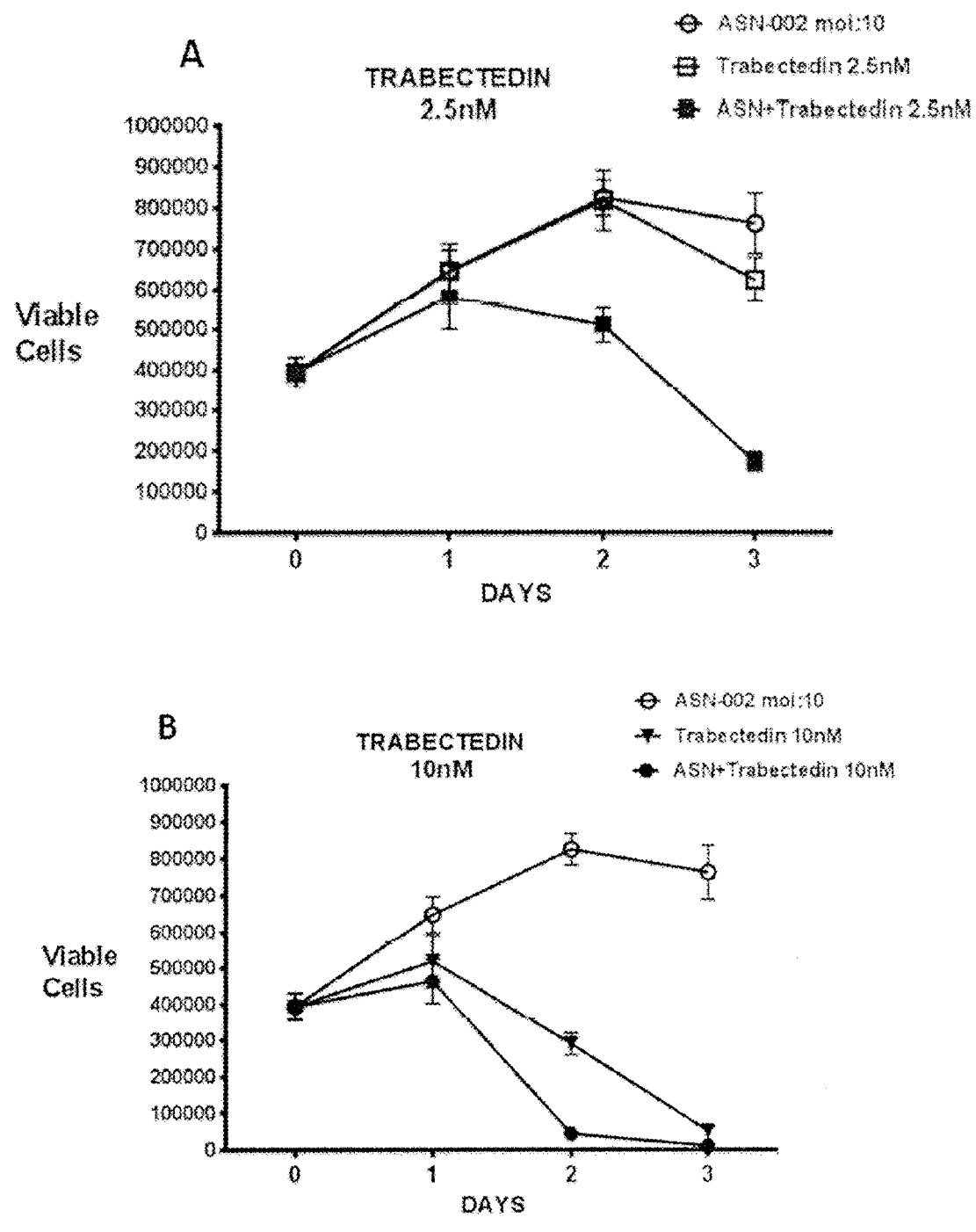

FIG. 14—Treatment of RIP3⁻ HeLa cells with a low dose of Trabectedin plus a low MOI of a replication-deficient recombinant adenovirus (ASN-002) expressing interferon gamma induces synergistic cell death. Line graphs illustrating cell death induced by Trabectedin, ASN-002 alone, or combined treatment of Trabectedin plus ASN-002 in cultured RIP3⁻ HeLa cells. (A) Trabectedin and ASN-002 added simultaneously to cells following a 48 hour exposure. (B) Trabectedin added to cells four hours after transduction with ASN-002. Combined treatment results in significantly greater cell death than cell death resulting from either treatment alone, or the expected cell death based on the sum of cell death resulting from the individual treatments.

Figure 15:
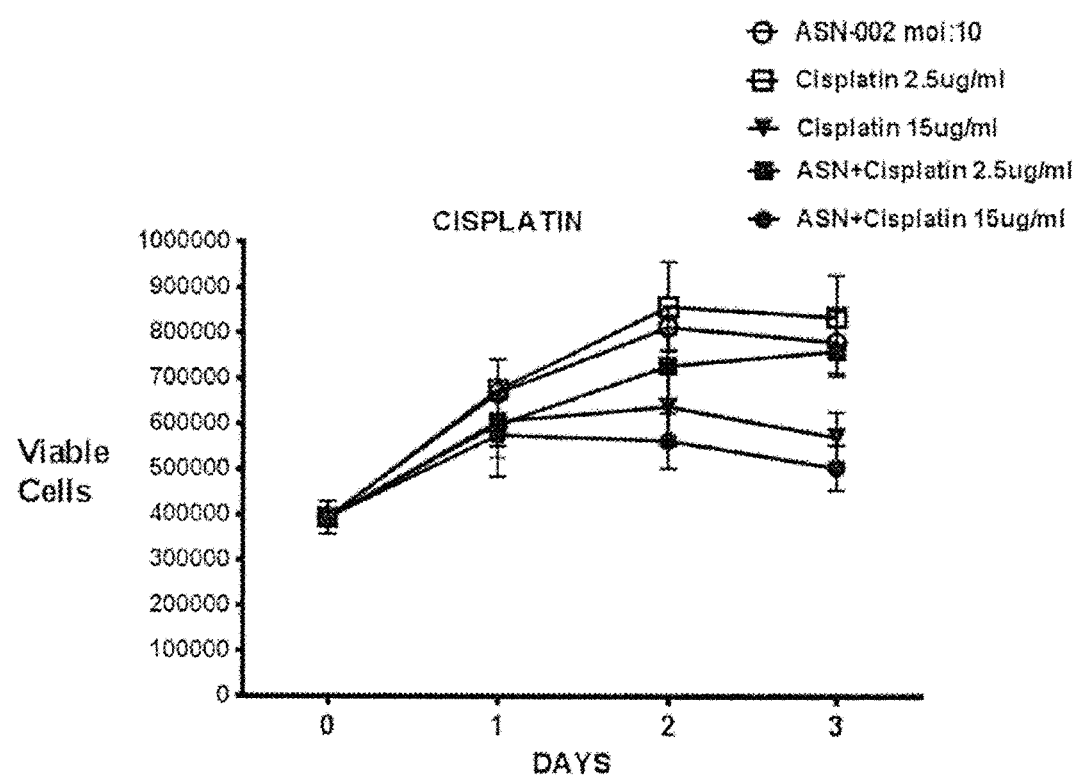

FIG. 15—Treatment of RIP3⁻ HeLa cells with a low dose of Cisplatin plus a low MOI of a replication-deficient recombinant adenovirus expressing interferon gamma (ASN-002) fails to induce synergistic cell death. Line graphs illustrating cell death induced by Cisplatin, ASN-002 alone, or combined treatment of Cisplatin plus ASN-002 in cultured RIP3⁻ HeLa cells following a 48 hour exposure. Combined treatment does not induce significantly greater cell death than treatment with Cisplatin or ASN-002 alone.

Figure 16:
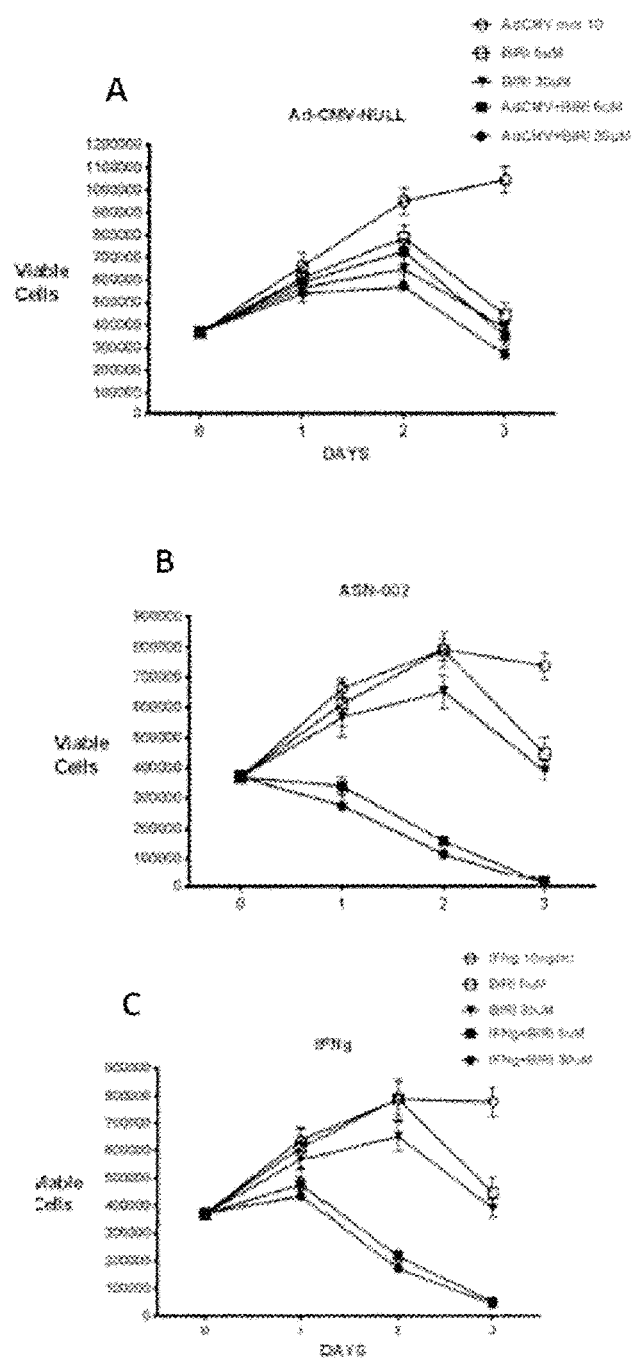

FIG. 16—Combination treatment synergy (Birinapant plus ASN-002) in RIP3⁻ HeLa cells depends on expression of IFN gamma from ASN-002 adenoviral vector. Line graphs illustrating cell death induced by treatment of HeLa (RIP3⁻) cells for 48 hours with: (A) Birinapant (5 µM or 30 µM) plus control adenovirus (AdCMV) not expressing IFN gamma; (B) Birinapant (5 µM or 30 µM) plus ASN-002 adenovirus expressing IFN gamma; and (C) Birinapant (5 µM or 30 µM) plus purified IFN gamma added to a concentration of 10 ng/ml. Combined treatment of Birinapant with either ASN-002 expressing IFN gamma or purified IFN gamma results in significantly greater cell death than cell death resulting from single agent treatment alone. In contrast, treatment with Birinapant in combination with control adenovirus not expressing IFN gamma induces the same level of cell death as Birinapant alone suggesting that cell death synergy observed in (B) and (C) depends on the presence of IFN gamma-not the presence of adenovirus itself.

FIG. 17—ASN-002 adenoviral vector-expressed IFN gamma or exogenous IFN gamma treatments in RIP3⁺ HeLa cells in the presence of inhibitors of apoptosis and necroptosis. Bar graphs illustrating cell death induced in RIP3⁺ (necroptosis-competent) HeLa cells in the presence of inhibitors of apoptosis and necroptosis by (A) AdCMV control adenovirus; (B) ASN-002 adenovirus expressing IFN gamma; and (C) purified IFN gamma.

FIG. 18—ASN-002 adenoviral vector-expressed IFN gamma or purified IFN gamma treatments in RIP3⁻ HeLa cells in the presence of an inhibitor of apoptosis. Bar graphs illustrating cell death induced in RIP3⁻ (necroptosis-deficient) HeLa cells in the presence of a pan caspase inhibitor of apoptosis by (A) AdCMV control adenovirus; (B) ASN-002 adenovirus expressing IFN gamma; and (C) purified IFN gamma.

FIG. 19—Trabectedin alone or in combination with ASN-002 or purified IFN gamma treatments in RIP3⁺ HeLa cells in the presence of inhibitors of apoptosis and necroptosis. Bar graphs illustrating cell death induced in RIP3⁺ (necroptosis-competent) HeLa cells in the presence of inhibitors of apoptosis and necroptosis by (A) Trabectedin plus AdCMV control adenovirus; (B) Trabectedin plus ASN-002 adenovirus expressing IFN gamma; (C) Trabectedin alone; and (D) Trabectedin plus purified IFN gamma.

Figure 20:
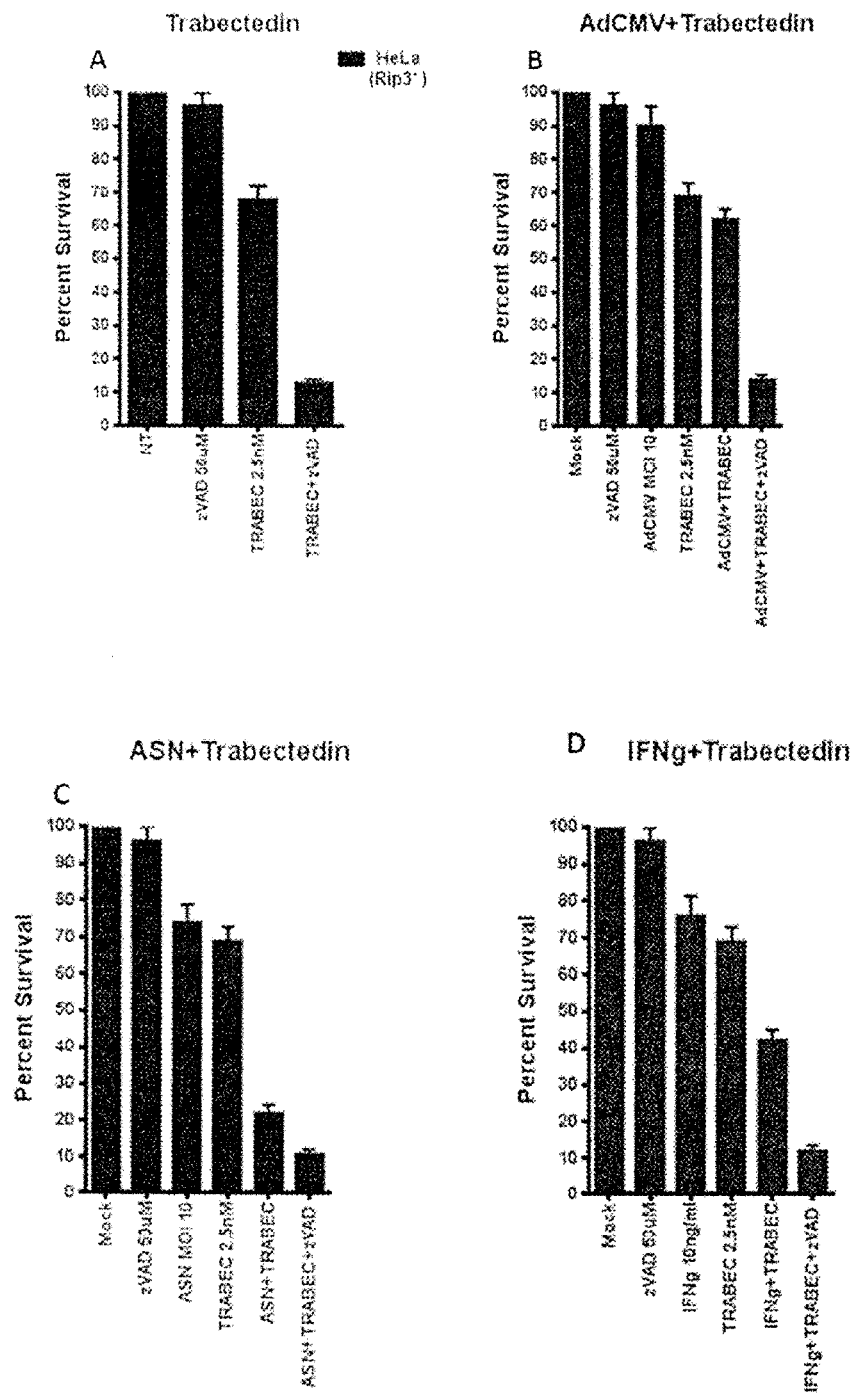

FIG. 20—Trabectedin alone or in combination with ASN-002 or purified IFN gamma treatments in RIP3⁻ HeLa cells in the presence of an inhibitor of apoptosis. Bar graphs illustrating cell death induced in RIP3⁻ (necroptosis-deficient) HeLa cells in the presence of a pan caspase inhibitor of apoptosis by (A) Trabectedin alone; (B) Trabectedin plus AdCMV control adenovirus; (C) Trabectedin plus ASN-002 adenovirus expressing IFN gamma; and (D) Trabectedin plus purified IFN gamma.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, cell biology, viral vector construction, gene therapy, molecular genetics, cancer biology, cancer therapy, immunology, pharmacology, protein chemistry, and biochemistry).

Unless otherwise indicated, the cell culture and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

The term "adverse event" as used herein, refers to any undesirable clinical occurrence in a subject/patient (as compared to the subject's baseline health) and is any untoward medical occurrence defined as an unintended disease or injury or untoward clinical signs (including abnormal laboratory findings) in a patient. More specifically, grades of adverse events, as referred to herein, include those published under the "Common Terminology Criteria for Adverse Events" published by the U.S. National Cancer Institute (version 4.03 published 14 Jun. 2010). These include mild (grade 1) adverse events which present as mild symptoms not requiring medical intervention; moderate (grade 2) adverse events, which require minimal, local or noninvasive intervention; severe or medically significant (grade 3) adverse events, which are not immediately life-threatening, but may require hospitalization or prolongation of hospitalization; life-threatening (grade 4) adverse events requiring urgent intervention; and adverse event-related death (grade 5). Adverse events commonly associated with cancer chemotherapy include, but are not limited to, fatigue, nausea, vomiting, diarrhea, alopecia, cutatenous toxicity, (e.g., skin rashes, pruritis, and mucositis), thrombocytopenia, anemia, ocular toxicity, bladder inflammation, sexual dysfunction and loss of fertility, cognitive dysfunction (e.g., short-term memory loss, loss of concentration, and loss of judgement), kidney toxicity, liver toxicity, and cardiotoxicity.

The term "antibody" as referred to herein, includes polyclonal antibodies, monoclonal antibodies, bispecific antibodies, fusion diabodies, triabodies, heteroconjugate antibodies, chimeric antibodies including intact molecules as well as fragments thereof, and other antibody-like molecules. Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain.

The term "caspase inhibitor," as used herein, includes caspases that are selective for one or multiple specific caspases (e.g., a caspase 3-selective inhibitor), or, alternatively, include pan caspase inhibitors that inhibit a broad range of caspases.

The term "chemotherapeutic agent" refers to a class of small molecules that is cytostatic and/or cytotoxic to cancer cells.

The terms "effective amount" or "therapeutically effective amount," as used herein, refer to a sufficient amount of an administered agent (e.g., a recombinant virus, a chemotherapeutic agent, a purified protein, or a caspase inhibitor) which will relieve to some extent one or more of the symptoms of the disease or condition being treated. The result can be reduction and/or alleviation of the signs, symptoms, or causes of a disease, or any other desired alteration of a biological system. A "therapeutically effective amount" of a therapeutic agent that is administered as part of a combination treatment can refer to an amount of the therapeutic agent that would be therapeutically effective when used on its own (i.e., as a monotherapy), or may refer to a reduced amount that is therapeutically effective by virtue of its combination with one or more additional therapeutic agents.

The term "nucleotide analogue chemotherapeutic agent or nucleotide precursor analogue chemotherapeutic agent," as used herein, refers to a class of antimetabolites that are structurally similar to purines, pyrimidines, and folic acid. Such agents act by inhibiting one or more enzymes that are critical for DNA synthesis, causing DNA damage and induction of apoptosis. Typically, such agents include a purine or pyrimidine ring and one or more non-naturally side groups on the ring that differ from the side groups found in a naturally occurring nucleotide. For the sake of brevity, this term will be referred to in abbreviated form as a "nucleotide analogue or nucleotide precursor analogue chemotherapeutic agent." A "non-nucleotide analogue or nucleotide precursor analogue chemotherapeutic agent," refers to a chemotherapeutic agent other than a nucleotide analogue chemotherapeutic agent or a nucleotide precursor analogue chemotherapeutic agent (e.g., a SMAC mimetic agent).

The term "purified," as used herein, in relation to a protein (e.g., "purified interferon gamma" and the like) refers to a protein provided in a form that is substantially free of contaminants normally associated with the protein in a native or natural environment.

The term "recombinant virus," as used herein, refers to any virus that is genetically modified by experimental intervention.

The term "refractory cancer," as used herein, refers to a cancer that becomes unresponsive to a particular chemotherapeutic agent over the course of its use in treatment.

The term "resistant cancer," as used herein, refers to a cancer that is initially responsive to a particular chemotherapeutic agent over a course of treatment, but then progresses and becomes unresponsive to the treatment with the chemotherapeutic agent during a period following treatment with the agent.

The term "small molecule," as used herein, refers to a chemical compounds or molecule having a molecular weight below 2000 daltons.

The terms "synergy" or "synergistic," as used herein refer to an effect (e.g., induction of cancer cell death) resulting from the use of a combination of agents where the effect is quantitatively greater than the sum of the effects resulting from the use of each agent separately. For example, if agent "A" causes 30% cell death and agent "B" causes 30% cell death, the (non-synergistic) sum of such effects would be 60%. If, in fact, the combination of agents A and B results in greater than 60% cell death, their combined effect would be considered synergistic.

The term "therapeutic agent," as used herein, refers to any molecule that plays a direct role in treating a cancer. Such therapeutic agents include by way of example only, a chemotherapeutic agent, an expressed biotherapeutic agent, a recombinant virus, a purified cytokine, an antibody, a caspase inhibitor, an immune response-inducing or enhancing agent, a purified polarising cytokine, and a purified chemokine.

The terms "treating" or "treatment," as used herein, refer to both direct treatment of a subject by a medical professional (e.g., by administering a therapeutic agent to the subject), or indirect treatment, effected, by at least one party, (e.g., a medical doctor, a nurse, a pharmacist, or a pharmaceutical sales representative) by providing instructions, in any form, that (i) instruct a subject to self-treat according to a claimed method (e.g., self-administer a drug) or (ii) instruct a third party to treat a subject according to a claimed method. Also encompassed within the meaning of the term "treating" or "treatment" are prevention of relapse or reduction of the disease to be treated, e.g., by administering a therapeutic at a sufficiently early phase of disease to prevent or slow its progression.

Combination Methods Including a Nucleotide Analogue or Nucleotide Precursor Analogue Chemotherapeutic Agent for Cancer Treatment The methods described herein include treating a human subject suffering from a cancer, by administering a combination regime of a chemotherapeutic agent and at least one other therapeutic agent, as described herein, to more effectively induce cancer cell death. Such combination therapies, as described herein, induce a synergistic level of cell death. In some embodiments a human subject is treated by administering a combination of at least a nucleotide analogue or nucleotide precursor analogue chemotherapeutic agent and a caspase inhibitor, which, as described herein, has been found to increase the level of cancer cell death compared to treatment with a chemotherapeutic alone.

Accordingly, provided herein is a method of treating a human subject suffering from a cancer, which method includes the steps of: (i) administering to the human subject a recombinant virus which expresses one or more biotherapeutic agents in the human subject; and (ii) administering to the human subject a chemotherapeutic agent, wherein the chemotherapeutic agent is a nucleotide analogue or a nucleotide precursor analogue. Optionally, this treatment method further includes administration of a caspase inhibitor as described herein.

Also provided herein is a method of treating a human subject suffering from a cancer, which method includes the steps of: (i) administering to the human subject a nucleotide analogue chemotherapeutic agent or a nucleotide precursor analogue chemotherapeutic agent; and (ii) administering to the human subject a caspase inhibitor.

Also provided herein is a method of treating cancer in a human subject, where the method includes the steps of: (i) administering to the human subject purified interferon gamma; and (ii) administering to the human subject a chemotherapeutic agent, wherein the chemotherapeutic agent is a nucleotide analogue or a nucleotide precursor analogue. Optionally, this method further includes administration of a caspase inhibitor as described herein.

Combination Methods Including a Chemotherapeutic Agent Other than a Nucleotide Analogue or Nucleotide Precursor Analogue Chemotherapeutic for Cancer Treatment Also provided herein is a method of treating a human subject suffering from a cancer, which method includes the steps of: (i) administering to the human subject a recombinant virus which expresses one or more biotherapeutic agents in the human subject; and (ii) administering to the human subject a chemotherapeutic agent other than a nucleotide analogue or a nucleotide precursor analogue. Optionally, this treatment method further includes administration of a caspase inhibitor as described herein.

Also provided herein is a method of treating a human subject suffering from a cancer, which method includes the steps of: (i) administering to the human subject a chemotherapeutic agent other than a nucleotide analogue or a nucleotide precursor analogue; and (ii) administering to the human subject a caspase inhibitor.

Also provided herein is a method of treating cancer in a human subject, where the method includes the steps of: (i) administering to the human subject purified interferon gamma; and (ii) administering to the human subject a chemotherapeutic agent other than a nucleotide analogue or a nucleotide precursor analogue. Optionally, this method further includes administration of a caspase inhibitor as described herein.

Cancers

Cancer that can be treated by the methods provided herein include, but are not limited to, acute lymphoblastic leukemia, acute myeloid leukemia, adrenocortical carcinoma, anal cancer, astrocytoma, basal cell carcinoma, bladder cancer, bone tumor, breast cancer, Burkitt's lymphoma, cervical cancer, chondrosarcoma, colorectal cancer, cutaneous T-cell lymphoma, endometrial cancer, esophageal cancer, Ewing's sarcoma, intraocular melanoma, retinoblastoma, gallbladder cancer, gastric (stomach) cancer, hairy cell leukemia, head and neck cancer, Hepatocellular (liver) cancer, Hodgkin lymphoma, Kaposi sarcoma, kidney cancer (renal cell cancer), laryngeal cancer, oral cancer, Liposarcoma, lung cancer, lymphomas, bone/osteosarcoma, melanoma, Merkel cell cancer, myeloma, neuroblastoma, ovarian cancer, pancreatic cancer, parathyroid cancer, prostate cancer, tectal cancer, renal cell carcinoma (kidney cancer), retinoblastoma, Ewing family of tumors, uterine cancer, skin cancer (non-melanoma), skin carcinoma, small intestine cancer, soft tissue sarcoma, squamous cell carcinoma, squamous neck cancer, stomach cancer, testicular cancer, throat cancer, thyroid cancer, thyroid cancer, and uterine cancer. In some preferred embodiments, the subject to be treated is suffering from a cancer selected from among colorectal cancer, basal cell carcinoma, breast cancer, colorectal cancer, ovarian cancer, cervical cancer, melanoma, non-melanoma skin cancer, gastric cancer, and pancreatic cancer. In some embodiments, the cancer to be treated include one or more tumours to be treated.

Symptoms, diagnostic tests, and prognostic tests for various types of cancers are known in the art. See, e.g., the website of the National Comprehensive Cancer Network (nccn.org/professionals/physician_gls/f_guidelines.asp).

In some embodiments, the subject to be treated by the methods described herein is a subject identified as suffering from a cancer that is refractory or resistant to treatment with chemotherapeutic agents alone (e.g., with a single chemotherapeutic agent or with multiple chemotherapeutic agents in combination). In some embodiments, the subject to be treated is a subject that was previously treated, unsuccessfully, for the cancer by administration of one or more chemotherapeutic agents alone. In other embodiments, the treatment methods described herein also include determining, prior to the treatment, whether a subject is suffering from a cancer that is refractory or resistant to treatment with chemotherapeutic agents alone.

Cell death is known to occur through a number of distinct, though often interconnected pathways, including: apoptosis, necroptosis, parthanatos, and autophagic cell death, though other, uncharacterized, cell death pathways are likely to exist. Apoptosis, a form of programmed cell death, can be initiated through one of two pathways—an intrinsic pathway by which the cell kills itself as a direct response to stress, and an extrinsic pathway by which the cell kills itself in response to signals received from its microenvironment. The two pathways both activate initiator caspases, which ultimately activate executioner caspases that kill the cells by degrading proteins indiscriminately. Necroptosis is a caspase-independent form of cellular suicide that often occurs in response to extrinsic signals associated with inflammation, e.g., signalling by certain cytokines such as TNF-alpha. RIPK3 plays a pivotal role in the execution of necroptosis. Parthanatos, another form of programmed cell death, is caused by the accumulation of poly(ADP-Ribose) or "PAR" and the nuclear translocation of apoptosis-inducing factor (AIF) from mitochondria. Parthanatos is also known as poly(ADP-Ribose) polymerase 1 (PARP-1)-dependent cell death. PARP-1 mediates parthanatos upon activation in response to extreme genomic stress and synthesizes PAR which causes nuclear translocation of AIF. Autophagic cell death, yet another distinct cell death pathway, is induced by extreme cell stress, and is characterized by cytoplasmic vacuolation (formation of autophagosomes) followed by excessive engulfment and degradation of organelles and other cytoplasmic components in lysosomes, which lead to cell death.

In some embodiments, cancer cells from a subject's cancer are tested to determine whether they are deficient in one or more known cell death pathways (e.g., apoptosis, necroptosis). Such a determination can include identifying mutations and/or deletions in genes known to play a role in a cell death pathway, e.g., a caspase in the apoptotic cell death pathway, and RIPK3 or RIPK1 in the necroptosis pathway. The identification of deletions or mutations in such genes indicates that the subject is unlikely to respond to conventional chemotherapeutic treatment alone, and/or is a suitable candidate for cancer treatment according to the methods described herein.

As will be appreciated by the skilled person in the art, depending on the particular cancer type to be treated both in terms of tissue specificity (e.g., melanoma) and mutational profile (e.g., caspase-8 deficient cancers or RIPK3-deficient cancers) the cell death pathways engaged by the treatment methods described herein may differ. The ability of the treatment methods described herein to engage multiple cell death pathways is thus likely to increase the likelihood of successful treatment of a cancer.

In some embodiments, the treatment methods described herein induce cancer cell death through at least one cell death pathway selected from among apoptosis, necroptosis, parthanatos, and autophagic cell death. In other embodiments, the treatment induces cell death through at least two cell death pathways selected from among apoptosis, necroptosis, parthanatos, and autophagic cell death. In some embodiments, the treatment method induces cancer cell death by necroptosis. In other embodiments, cancer cell death is induced by at least apoptosis and necroptosis. In further embodiments the treatment method induces cancer cell death by at least one pathway other than apoptosis or necroptosis (e.g., parthanatos, autophagic cell death, or another cell death pathway).

In some embodiments, the subject to be treated is suffering from a cancer containing at least some cells that are deficient in a caspase-dependent cell death pathway. For example, such cells may be deficient (including heterozygous or homozygous loss of function) in expression or function of one or more Caspases, e.g., Caspase 8, Caspase 3, Caspase 10, Caspase 2, Caspase 6, or Caspase 7. In some embodiments, the cancer cells deficient in caspase-dependent cell death pathway are deficient in expression or function of a caspase or FADD. In other embodiments, the cancer contains cells that are deficient in a necroptotic cell death pathway. In some embodiments, cancer cells deficient in a necroptotic cell death pathway are deficient in the expression or function of RIPK1, RIPK3, or MLKL. In some embodiments, the cancer contains cells that are deficient in a parthanatos cell death pathway (e.g., PARP-1 deficient cancer cells). In other embodiments, the cancer contains cells that are deficient in an autophagic cell death pathway (e.g., cancer cells deficient in AMBRA1, ATG12, ATG16L1, or ATG4A). In some embodiments, the cancer to be treated contains cancer cells deficient in multiple cell death pathways selected from among apoptosis, necroptosis, parthanatos, and autophagic cell death. Mutations in various candidate cancer genes and methods for their identification are described in, e.g., Lawrence et al (2014), Stacey et al (2015), and Bonilla et al (2016). Techniques for identifying the presence of such deficient cells is known in the art, e.g., by single cell isolation and sequencing as reviewed in Navin (2014) and Gawad et al (2016).

Nucleotide Analogue and Nucleotide Precursor Analogue Chemotherapeutic Agents

Chemotherapeutic agents used in the cancer treatment methods described herein are nucleotide analogue or nucleotide precursor chemotherapeutic agents. Suitable nucleotide analogue or nucleotide precursor analogue chemotherapeutic agents include, but are not limited to, Fluorouracil, Azacitidine, Azathioprine, Capecitabine, Cladribine, Clofarabine, Cytarabine, Decitabine, Emtricitabine, Doxifluridine, Fludarabine, Gemcitabine, Mercaptopurine, Nelarabine, Thioguanine, or any combination thereof.

In some embodiments, the nucleotide analogue or nucleotide precursor analogue chemotherapeutic agent to be administered includes one or more of Fluorouracil, Capecitabine, Gemcitabine, and Doxifluridine.

In some preferred embodiments, of a nucleotide chemotherapeutic agent to be used in the treatment method is Fluorouracil or an active structural analogue thereof, e.g., Capecitabine. In some preferred embodiments the nucleotide analogue chemotherapeutic agent is Fluorouracil.

Non-Nucleotide Analogue Chemotherapeutic Agents

In some embodiments chemotherapeutic agents other than nucleotide analogue or nucleotide precursor analogue chemotherapeutic agents are of a class selected from among DNA-binding agents, second mitochondrial-derived activator of caspases (SMAC) mimetics, alkylating agents, topoisomerase inhibitors, nucleoside analogs, proteasome inhibitors, and poly ADP ribose polymerase (PARP) inhibitors.

In some embodiments the non-nucleotide analogue chemotherapeutic agent to be used is a DNA-binding chemotherapeutic agent. In some embodiments, where the chemotherapeutic agent to be used is a DNA-binding chemotherapeutic agent, the chemotherapeutic agent is selected from among Trabectedin, Dactinomycin, Epirubicin, and Mitomycin C. In some preferred embodiments the DNA-binding chemotherapeutic agent to be administered is Trabectedin.

In other embodiments the treatment method includes administering a SMAC mimetic chemotherapeutic agent. Suitable SMAC mimetic chemotherapeutic agents include, but are not limited to, Birinapant (AKA TL32711; CAS 1260251-31-7)), LCL-161 (Novartis; CAS 1005342-46-0), GDC-0152 (Genentech; CAS 873652-48-3), GDC-0917/ CUDC-427 (Genentech; CAS 1446182-94-0), SM-406/AT-406 (CAS 1071992-99-8), BV6 (CAS 1001600-56-1), and any combination thereof. In some embodiments a SMAC chemotherapeutic agent is administered in combination with a different class of chemotherapeutic agent. In some preferred embodiments, the administered SMAC mimetic chemotherapeutic agent to be administered is Birinapant.

In some embodiments the chemotherapeutic agent to be administered is a topoisomerase inhibitor. Suitable topoisomerase inhibitor chemotherapeutic agents include, but are not limited to, Doxorubicin, Amsacrine, Etoposide, Etoposide phosphate, Teniposide, Irinotecan, Topotecan, Camphothecin, or any combination thereof.

In some embodiments the chemotherapeutic agent to be administered is a an alkylating agent. In some embodiments the alkylating agent is selected from from among Mechlorethamine, Ifosamide, Uramustine, Carmustine, Busulfan, and any combination thereof.

In other embodiments the therapeutic agent to be administered includes a poly ADP ribose polymerase (PARP). In some embodiments the PARP inhibitor chemotherapeutic agent is selected from among Olaparib (AZD-2281; CAS 763113-22-0), Veliparib (ABT-888; CAS 912445-05-7), Talazoparib (BMN 673; CAS 1207456-01-6), Niraparib (MK-4827; CAS No:1038915-60-4), and any combination thereof.

In yet other embodiments the therapeutic agent to be administered includes a proteasome inhibitor chemotherapeutic agent. In some embodiments the proteasome inhibitor chemotherapeutic agent is selected from among Bortezomib (CAS 179324-69-7), Carfilzomib (CAS 868540-17-4), NPI-0052 (CAS 437742-34-2), MLN9708 (CAS 1201902-80-8), CEP-18770 (CAS 847499-27-8), ONX0912 (CAS 935888-69-0), and any combination thereof.

Recombinant Viruses

A variety of recombinant virus types are suitable for expression of one or more biotherapeutic agents for the combination cancer treatment methods described herein.

In some embodiments, the recombinant virus to be administered is a DNA virus. Suitable types of DNA viruses include adenovirus, adeno-associated virus (AAV), herpes simplex virus (HSV), retrovirus, and lentivirus. Methods for design, production, and use of such types of recombinant DNA viruses are established in the art, as exemplified in Fukazawa et al (2010) and in "Gene Therapy Protocols" for adenovirus; "Adeno-Associated Virus: Methods and Protocols" for AAV; Cody et al (2013) and "Herpes Simplex Virus: Methods and Protocols" for HSV; "Gene Therapy Protocols Vol. 1: Production and In Vivo Applications of Gene Transfer Vectors" and Amer (2014) for retrovirus; and Merten et al (2016) and Emeagi et al (2013) for lentivirus. In some preferred embodiments, the recombinant virus to be used in the treatment method is an adenovirus. In other preferred embodiments the recombinant virus is a lentivirus.

In other embodiments, the recombinant virus to be administered is a recombinant, replication-deficient or replication-competent RNA virus. Suitable types of replication deficient or replication-competent RNA viruses Alphavirus (e.g., Sindbis or Semliki Forest Virus), Flavivirus (e.g., Kunjin virus), Paramyxovirus (e.g., Sendai virus), Rhabdovirus (e.g., vesicular stomatitis virus), and Orthomyxovirus (e.g., influenza A virus). Methods for design, production, and use of such types of recombinant RNA viruses are established in the art, as exemplified in Lundstrom (2015) and Quetglas et al (2010) for Alphavirus; Hoang-Le et al (2009) and Usme-Ciro et al (2013) for Flavivirus; Cattaneo (2010) for Paramyxovirus; Finke et al (2005) and Chang et al (2010) for Rhabdovirus; and U.S. Pat. No. 8,475,806 for Orthomyxovirus.

In some embodiments, the recombinant DNA or RNA virus is a replication deficient virus incapable of replication in transduced cells. In other embodiments, the recombinant virus is a replication-competent virus, which can replicate in a transduced host cell. Alternatively, the recombinant virus is a conditionally replication-competent virus that can replicate only in particular cell types or in cells with a particular expression profile, e.g., p53-deficient cancer cells.

Examples of suitable promoters for driving expression of biotherapeutic agents from a recombinant virus in a method described herein include, but are not limited to, constitutive promoters such as, CMV, CAG, EF-1-α, HSV1-TK, SV40, β-actin, and PGK promoters. In other embodiments, a promoter is an inducible promoters, such as those containing TET-operator elements. In certain embodiments, target-selective promoters are used to drive expression of biotherapeutic agents in specific cell types or specifically in cancer cells. Examples of suitable cancer/cell type-selective promoters useful for the methods described herein include, but are not limited to, the erb 2 promoter (breast cancer), the carcinoembryonic antigen promoter (colorectal cancer), the urokinase-type plasminogen activator receptor promoter (colorectal cancer), the tyrosinase promoter (melanoma), the melacortin receptor (melanoma); the human telomerase reverse transcriptase (hTERT) promoter (multiple cancers), the RAS-related nuclear protein promoter (multiple cancers), the breast cancer metastasis suppressor 1 promoter (multiple cancers), the Rad51C promoter (multiple cancers), and the minichromosome maintenance complex component 5 promoter (multiple cancers).

In some embodiments, where two or more proteins are to be expressed from a recombinant virus, the recombinant virus contains an expression cassette encoding a polycistronic mRNA (a "polycistronic expression cassette"), which, upon translation gives rise to independent polypeptides comprising different amino acid sequences or functionalities. In some embodiments, a polycistronic expression cassette encodes a "polyprotein" comprising multiple polypeptide sequences that are separated by encoded by a picornavirus, e.g., a foot-and-mouth disease virus (FMDV) viral 2A peptide sequence. The 2A peptide sequence acts co-translationally, by preventing the formation of a normal peptide bond between the conserved glycine and last proline, resulting in ribosome skipping to the next codon, and the nascent peptide cleaving between the Gly and Pro. After cleavage, the short 2A peptide remains fused to the C-terminus of the 'upstream' protein, while the proline is added to the N-terminus of the 'downstream' protein. which during translation allow cleavage of the nascent polypeptide sequence into separate polypeptides. See, e.g., Trichas et al (2008).

In other embodiments, a polycistronic expression cassette may incorporate one or more internal ribosomal entry site (IRES) sequences between open reading frames incorporated into the polycistronic expression cassette. IRES sequences and their use are known in the art as exemplified in, e.g., Martinez-Sales (1999).

In some embodiments, a recombinant virus used in the method has targeted tropism, e.g., tropism for a particular cell type as reviewed in Bucholz et al (2015). Suitable targeting moeities, to be incorporated into a recombinant viral capsid surface, include ligands that bind to cell surface receptors that are overexpressed by cancer cells. For example, the Her2/neu receptor, frequently overexpressed in breast cancer cells, can be targeted by incorporating a designed ankryrin repeat protein (DARPin) ligand, as has been done for lentivirus (Munch et al 2011) in AAV (Munch et al 2013). In another example a recombinant lentivirus is designed to target P-glycoprotein, overexpressed on the surface of melanoma cells, by incorporating an antibody into the viral capsid surface (Morizono et al 2005).

Expressed Biotherapeutic Agents

Biotherapeutic agents suitable for the methods described herein include biological molecules that can be genetically encoded and expressed by use of an expression vector, e.g., a recombinant virus. Thus, biotherapeutic agents include peptides, proteins, as well as non-coding RNAs such as short hairpin RNAs (shRNAs), microRNAs (miRNAs), miRNA inhibitors, antisense RNAs. Preferably, the biotherapeutic agents to be expressed have highest sequence identity to a human homolog. In some preferred embodiments, the sequence of a biotherapeutic agent to be expressed comprises the sequence of the human homolog of (e.g., the amino acid sequence of human IFN gamma or the human nucleic acid sequence encoding human IFN gamma). In some embodiments the sequence of the biotherapeutic agent to be expressed is at least about 80% identical to the human homolog, e.g., 82%, 85%, 88%, 90%, 92%, 95%, 97%, 99%, or another percent identical to the human homolog sequence ranging from about 80% to 100% identical to the human homolog sequence.

In some embodiments, a biotherapeutic agent to be expressed includes a peptide or protein to be expressed. Suitable types of protein biotherapeutic agents to be expressed include, but are not limited to a cytokine, a protein regulating apoptotic cell death, a protein regulating necroptotic cell death, a protein regulating parthanatos cell death, or a protein regulating autophagic cell death, or an agonist which binds a cell receptor and activates cell death by apoptosis, necroptosis, parthanatos, autophagic cell death, or any combination thereof.

In some embodiments, a biotherapeutic agent to be expressed by the recombinant virus used in the treatment method is a cytokine. Suitable cytokines to be expressed include, but are not limited to, interferon gamma, interferon alpha, B-cell activating factor (BAFF), TL1, TNF alpha, TRAIL, lymphotoxin alpha, lymphotoxin beta, OX-40 ligand, LIGHT (also known as tumor necrosis factor superfamily member 14), FAS-ligand, 4-1BB ligand, RANK ligand, CD30 ligand, CD40 ligand, glucocorticoid-induced TNFR-related protein ligand (GITRL), or any combination thereof. In some preferred embodiments, the cytokine to be expressed is interferon gamma.

In other embodiments, the biotherapeutic agent to be expressed is a protein regulating apoptotic cell death. Suitable proteins regulating apoptotic cell death include, but are not limited to, Fas-Associated protein with Death Domain (FADD; GenBank NP_003815.1), Bcl-2-associated death promoter (BAD; GenBank NP_004313.1), Bcl-2-associated X protein (BAX; GenBank NP_001278357.1), BH3 interacting-domain death agonist (BID; GenBank NP_001187.1), Bcl-2-like protein 11 (BIM; GenBank NP_001191035.1), Bcl-2 homologous antagonist killer (BAK; GenBank NP_001179.1), Cytochrome c (GenBank NP_061820.1), Apoptotic protease activating factor 1(APAF1; GenBank NP_001151.1), Death domain-containing protein (CRADD; GenBank NP_003796.1), TNF, Tumor necrosis factor receptor 1 (TNFR1; GenBank NP_001056.1), Abelson murine leukemia viral oncogene homolog 1 (ABL1; GenBank NP_005148.2), cell death-inducing DFFA-like effector a (CIDEA; GenBank NP_001270.1), Cell death-inducing DFF45-like effector b (CIDEB; GenBank NP_055245.2), tumour protein p53 (TP53; GenBank NP_000537.3), tumour protein p73 (TP73; GenBank NP_001119712.1), CASP8 and FADD-like apoptosis regulator (CFLAR; GenBank NP_001120655.1), Death-associated protein kinase 1 (DAPK1; GenBank NP_001275658.1), tumor necrosis factor receptor superfamily member 25 (TNFRSF25; GenBank NP_001034753.1), B-cell lymphoma/leukemia 10 (BCL10; GenBank NP_003912.1), Bcl-2-like protein 11 (BCL2L11; GenBank NP_001191035.1), Bcl-2-associated transcription factor 1 (BCLAF1; GenBank NP_001070908.1), BCL2/Adenovirus E1B 19 kDa Interacting Protein 1 (BNIP1; GenBank NP_001196.2), BCL2/adenovirus E1B 19 kDa protein-interacting protein 3BNIP3 (GenBank NP_004043.3), CD27 (GenBank NP_001233.1), CD70 (GenBank NP_001243.1), DNA fragmentation factor subunit alpha (DFFA; GenBank NP_004392.1), Fas cell surface death receptor (FAS; GenBank NP_000034.1), Fas Ligand (FASLG; GenBank NP_000630.1), Growth arrest and DNA-damage-inducible protein (GADD45A; GenBank NP_001186670.1), Activator of Apoptosis Harakiri (HRK; GenBank NP_003797.1), Lymphotoxin alpha (LTA; GenBank NP_000586.2), Bcl-2-modifying factor (BMF; GenBank NP_001003940.1), Nucleotide-binding oligomerization domain-containing protein 1 (NOD1; GenBank NP_006083.1), NADPH oxidase activator (NOXA; GenBank NP_066950.1), p53 upregulated modulator of apoptosis (PUMA; NP_001120712.1), Apoptosis-associated speck-like protein containing a caspase-recruitment domain (PYCARD; GenBank NP_037390.2), Tumor necrosis factor receptor superfamily member 10A (TNFRSF10A; GenBank NP_003835.3), Tumor necrosis factor superfamily member 10 (TNFSF10; GenBank NP_001177871.1), Tumor necrosis factor receptor superfamily member 9 (TNFRSF9; GenBank NP_001552.2), Tumor necrosis factor superfamily member 8 (TNFSF8; GenBank NP_001235), Tumor suppressor p53-binding protein 2 (TP53BP2; GenBank NP_001026855.2), Tumor necrosis factor receptor type 1-associated DEATH domain protein (TRADD; GenBank NP_003780.1), TNF Receptor-Associated Factor-3 (TRAF3; GenBank NP_001186356.1), or any combination thereof.

In some embodiments, the biotherapeutic agent to be expressed is a protein regulating necroptotic cell death. Suitable proteins regulating necroptotic cell death include, but are not limited to, DNA-dependent activator of interferon regulatory factors (DAI; GenBank NP_001153889.1), Receptor-interacting serine/threonine-protein kinase 3 (RIPK3 AKA "RIP3"; GenBank NP_006862.2), Mixed lineage kinase domain-like protein (MLKL; GenBank NP_689862.1), Second mitochondria-derived activator of caspases (SMAC; GenBank NP_063940.1), TIR-domain-containing adapter-inducing interferon beta (TRIF; GenBank NP_891549), or any combination thereof. In preferred embodiments the protein regulating necroptotic cell death is selected from among DAI, RIPK1, RIPK3, MLKL, and TRIF. In some embodiments, the protein regulating necroptotic cell death is a fusion protein that presents RIPK3 or RIPK1 in a dimeric or oligomeric form, as described in, e.g., Cook et al (2014) and Orozco et al (2014).

In further embodiments the biotherapeutic agent to be expressed is a protein regulating parthanatos cell death. Suitable proteins regulating parthanatos cell death include Poly [ADP-ribose] polymerase 1 (PARP1; GenBank NP_001609.2), Apoptosis-inducing factor 1, mitochondrial (AIFM1, GenBank NP_004199.1), or a combination thereof.

In yet other embodiments the biotherapeutic agent to be expressed is a protein regulating autophagic cell death. Suitable proteins regulating autophagic cell death include, but are not limited to, Activating molecule in BECN1-regulated autophagy protein 1 (AMBRA1, GenBank NP_060219.2), Autophagy-related protein 12 (ATG12, GenBank NP_004698), Autophagy-related protein 16-1 (ATG16L1, GenBank NP_110430.5), Cysteine protease ATG4A (ATG4A; GenBank NP_443168.2), Cysteine protease ATG4B (ATG4B; GenBank NP_037457.3), Autophagy related 4C, cysteine peptidase (ATG4C; GenBank NP_835739.1), Autophagy related 4D, cysteine peptidase (ATG4D; GenBank NP_116274.3), Autophagy protein 5 (ATG5; GenBank NP_001273035.1), Autophagy-related protein 9A (ATG9A; GenBank NP_001070666.1), Autophagy-related protein 9B (ATG9B; GenBank AAI28588.1), Beclin-1 (BECN1; GenBank NP_001300927.1), Gamma-aminobutyric acid receptor-associated protein (GABARAP; GenBank NP_009209.1), GABA(A) receptor-associated protein like 1 (GABARAPL1; GenBank CAG38511.1), GABA type A receptor associated protein like 2 (GABARAPL2; GenBank NP_009216.1), Immunity-related GTPase family M protein (IRGM; GenBank NP_001139277.1), Microtubule-associated proteins 1A/1B light chain 3A (MAP1LC3A; GenBank NP_115903.1), Microtubule-associated proteins 1A/1B light chain 3B (MAP1LC3B; GenBank NP_073729.1), Regulator of G-protein signaling 19 (RGS19; GenBank NP_001034556.1), Serine/threonine-protein kinase ULK1 (ULK1; GenBank NP_003556.1), Autophagy-related protein 10 (ATG10; GenBank NP_113670.1), Autophagy related 16-like 2 protein (ATG16L2; GenBank AAI46661.1), Autophagy-related protein 3 (ATG3; GenBank NP_071933.2), Autophagy-related protein 7 (ATG7; GenBank NP_006386.1), Autophagy-related protein 9A (ATG9A; GenBank NP_076990.4), ras-related protein 24 (RAB24; GenBank NP_001026847.1), DNA damage-regulated autophagy modulator protein 1 (DRAM1; GenBank NP_060840.2), Family with sequence similarity 176, member A protein (FAM176A; GenBank AAH63016.1), or any combination thereof.

In some embodiments, the biotherapeutic agent to be expressed is an agonist antibody to the FAS receptor (FasR), e.g., a scFv antibody such as the "E09" scFv antibody described in Chodorge et al (2012).

In other embodiments, a biotherapeutic agent to be expressed by a recombinant virus used in the treatment method includes a non-coding RNA. Such non-coding RNAs include short hairpin RNAs (shRNAs) to effect RNA interference, microRNAs (miRNAs), miRNA inhibitors, antisense RNAs including antisense RNAs against miRNAs (e.g., "miRNA sponges" as described in Ebert et al 2007).

The terms "RNA interference" refers generally to a process in which a double-stranded RNA molecule reduces the expression of a nucleic acid sequence with which the double-stranded RNA molecule shares substantial or total homology. However, it has more recently been shown that RNA interference can be achieved using non-RNA double stranded molecules (see, for example, US 20070004667).

By "shRNA" or "short-hairpin RNA" is meant an RNA molecule where less than about 50 nucleotides, preferably about 19 to about 23 nucleotides, is base paired with a complementary sequence located on the same RNA molecule, and where said sequence and complementary sequence are separated by an unpaired region of at least about 4 to about 15 nucleotides which forms a single-stranded loop above the stem structure created by the two regions of base complementarity.

Included shRNAs are dual or bi-finger and multi-finger hairpin dsRNAs, in which the RNA molecule comprises two or more of such stem-loop structures separated by single-stranded spacer regions.

Once designed, the nucleic acid molecules comprising a double-stranded region can be expressed in vivo, preferably by the use of transduction with recombinant expression viruses.

In some embodiments, a non-coding RNA to be expressed as a biotherapeutic agent is an shRNA against a cancer target. Suitable shRNA cancer targets include, but are not limited to, Cyclin D1 (GenBank BC023620.2), Class III β-tubulin (GenBank NM_006086), Receptor for activated C-kinase 1 (RACK1; GenBank NM006098); Ras homolog gene family member A (RHOA; GenBank BC001360), Mitogen-activated protein kinase-activated protein kinase 5 (MAPKAPK5; GenBank NM003668); Growth differentiation factor-11 (GDF11; GenBank AF028333), Engrailed 1 (EN1; GenBank NM_001426.3), and Microphthalmia-associated transcription factor (MITF; GenBank NM_000248).

In other embodiments, a non-coding RNA to be expressed is a miRNA. Suitable examples of a miRNA to be expressed in a treatment method described herein include, but are not limited to, mir-491, mir-133a, mir-204, let 7 miRNA, mir-24, mir-15a, mir-16, mir-26a, mir-148b, mir-199a-3p, mir-512, mir-874a, or any combination thereof. Suitable examples of suitable miRNA targets for suppression in cancer cells, e.g., by expression of an miRNA sponge, include, but are not limited to mir-223, mir-211, mir-10b, mir-9, mir-17-92, mir-103, mir-106b, mir-107 mir-155, mir-21, mir-128, or any combination thereof.

In certain embodiments a recombinant virus to be used in the treatment method expresses at least two biotherapeutic agents, e.g., two proteins; a non-coding RNA and a protein; or two non-coding RNAs.

In some preferred embodiments, the two biotherapeutic agents to be expressed include a cytokine and a protein selected from among MLKL, SMAC, the N-terminal tetrapeptide (AVPI) of SMAC (Guo et al 2002), BAX, DAI, cyclic GMP-AMP synthase (cGAS; GenBank NP_612450.2), and RIPK3.

Combinations with Immune Response-Inducing Agents, Immune Response-Enhancing Agents, and/or Checkpoint Inhibitor Antibodies In some embodiments, of any of the above treatment methods the method further includes administration of one or more immune response-inducing agent or immune response enhancing agent to augment cancer cell death through a subject's immune response.

In some preferred embodiments, administration of one or more immune response-inducing agents includes: (i) a purified polarising cytokine or purified chemokine; and (ii) a purified pro-inflammatory agent. Purified polarising cytokines act to induce maturation of naïve T-cells into mature T helper cell type 1 (Th1) and/or Th2 cells to promote an immune response against cancer cells.

In some embodiments, a purified polarising cytokine to be administered is selected from among IL-12, IL-15, IL-18, IL-21, IL-23, IL-27, and a combination thereof. In some embodiments, the purified chemokine is selected from among CXCL1, CCL25, CCL27, and a combination thereof.

In some embodiments, the one or more immune response-inducing agents include an agonist for a receptor selected from among 4-1BB, OX40, CD70, ICOS, and CD40.

In some embodiments, the purified pro-inflammatory agent includes a toll-like receptor (TLR) agonist. Suitable TLR agonists include, but are not limited to, Poly I:C, Poly A:U, lipopolysaccharides, Mannans, CpG, Resiquimod, Imiquimod, Glycoinositolphospholipids, or any combination thereof. In other embodiments, the purified pro-inflammatory agent is Ingenol mebutate (CAS 75567-37-2).

In other embodiments, where the treatment method includes administering an immune response enhancing agent, the immune response-enhancing agent includes an anti-IL10 antibody, an anti-IL10 receptor antibody, an anti-IL4 antibody, an anti-IL4 receptor antibody, or any combination thereof.

In further embodiments, the treatment method includes administration of an immune checkpoint inhibitor. Examples of suitable immune checkpoint inhibitors to be administered include, but are not limited to an antibody against Programmed Death (PD-1), an antibody against PD-Ligand 1 (PDL-1), an antibody against Cytotoxic T-Lymphocyte-Associated protein 4 (CTLA-4), an antibody against Adenosine A2A receptor (A2AR), an antibody against B and T Lymphocyte Attenuator (BTLA), an antibody against Cytotoxic T-Lymphocyte-Associated protein 4 (CTL-4), an antibody against indoleamine 2,3-dioxygenase (IDO), an antibody against Lymphocyte Activation Gene-3 (LAG3), and an antibody against T-cell immunoglobulin domain, Mucin domain 3 (TIM-3), an antibody against killer-cell immunoglobulin-like receptor (KIR), an antibody against CD94, an antibody against Leukocyte-associated immunoglobulin-like receptor 1 (LAIR-1), antibodies against against any of Leukocyte immunoglobulin-like receptor subfamily A (LILRA) members 1-6 (LILRA1-LILRA6), antibodies against any of Leukocyte immunoglobulin-like receptor subfamily B (LILRB) members 1-5, or any combination thereof.

Dosing Regimes for Nucleotide Analogue and Nucleotide Precursor Analogue Chemotherapeutic Agents The combination treatment methods disclosed herein achieve a synergistic effect. Accordingly, in preferred embodiments the dose of a chemotherapeutic agent (e.g., a nucleotide analogue chemotherapeutic agent such as Fluorouracil), the dose of a recombinant virus, the dose of purified interferon gamma, or both in a combination treatment may be reduced relative to a standard dose accepted in the art for administration of each agent alone. In some embodiments, of the treatment methods described herein a reduced dose avoids induction of more than a moderate adverse event in the subject being treated. In some preferred embodiments, the dose to be administered is reduced by about 25% to about 95% relative to a standard dose, e.g., a 30%, 35%, 40%, 50%, 60%, 70%, 75%, 80%, 85%, 90%, or another percent dose reduction relative to a standard dose for the cancer to be treated in a range of about 25% to about 95%. In some preferred embodiments, the dose is reduced by about 50% to about 85% relative to the a standard dose.

In preferred embodiments, e.g., skin cancers and others forms of cancer that present with lesions/tumours amenable to direct local administration (e.g., melanoma), administration is intralesional administration. In some preferred embodiments, the method includes intralesional administration of Fluorouracil. In some embodiments, intralesional administration of Fluorouracil ranges from about 0.02 mg/lesion to about 10 mg/lesion per administration, e.g., about 0.05 mg/lesion, 0.075 mg/lesion, 0.1 mg/lesion, 0.15 mg/lesion, 0.2 mg/lesion, 0.25 mg/lesion, 0.3 mg/lesion, 0.5 mg/lesion, 0.7 mg/lesion, 0.8 mg/lesion, 1 mg/lesion, 1.5 mg/lesion, 2 mg/lesion, 3 mg/lesion, 3.5 mg/lesion, 4 mg/lesion, 4.5 mg/lesion, 5 mg/lesion, 5.5 mg/lesion, 6 mg/lesion, 7 mg/lesion, 8 mg/lesion, 9 mg/lesion or another intralesional dose from about 0.02 mg/lesion to about 10 mg/lesion per administration. In some preferred embodiments, the intralesional dose of Fluorouracil ranges from about 2.5 mg/lesion to about 10 mg/lesion.

In some embodiments, a cancer to be treated includes treatment by systemic administration of a nucleotide analogue or nucleotide precursor analogue chemotherapeutic agent as described in the combination treatment methods provided herein. In other embodiments, the administration is intraperitoneal administration. In some embodiments, the administration is intrapleural administration. In some embodiments, where the Fluorouracil is administered by systemic, intraperitoneal, or intrapleural administration, the administered dose is in a range of about 0.01 mg/kg to about 5 mg/kg per administration, e.g., 0.015 mg/kg, 0.02 mg/kg, 0.03 mg/kg, 0.04 mg/kg, 0.05 mg/kg, 0.06 mg/kg, 0.07 mg/kg, 0.08 mg/kg, 0.1 mg/kg, 0.12 mg/kg, 0.13 mg/kg, 0.15 mg/kg, 0.17 mg/kg, 0.20 mg/kg, 0.22 mg/kg, 0.25 mg/kg, 0.27 mg/kg, 0.3 mg/kg, 0.4 mg/kg, 0.5 mg/kg, 0.75 mg/kg, 0.9 mg/kg, 1 mg/kg, 1.5 mg/kg, 2 mg/kg, 2.5 mg/kg, 3 mg/kg, 4 mg/kg or another dose ranging from about 0.1 mg/kg to about 5 mg/kg. In some preferred embodiments, the dose of Fluorouracil is about 0.01 mg/kg to about 2 mg/kg.

In other embodiments, treatment of a cancer (e.g., a skin cancer) includes topical administration of Fluorouracil. In some embodiments, Fluorouracil is administered topically as a formulation ranging from about 0.01% (w/v) to about 3% (w/v), e.g., 0.02%, 0.03%, 0.04%, 0.05%, 0.08%, 0.1%, 0.2%, 0.3%, 0.4%, 0.5%, 0.6%, 0.7%, 0.8%, 1%, 1.2%, 1.3%, 1.5%, 1.7%, 2%, 2.2%, 2.5%, 2.8%, or another topical concentration from about 0.01% (w/v) to about 3% (w/v). In some embodiments, the topical Fluorouracil concentration is about 0.02% (w/v) to about 2%. In preferred embodiments the topical Fluorouracil concentration is about 0.1% to about 0.5%.

In other embodiments, where administration of the chemotherapeutic agent is intralesional, the total aggregate dose per treatment cycle for a nucleotide analogue chemotherapeutic agent (e.g., Fluorouracil) ranges from about 1 mg/lesion to about 125 mg/lesion per total aggregate dose per treatment cycle, e.g., about 1.5 mg/lesion, 2 mg/lesion, 3 mg/lesion, 5 mg/lesion, 7 mg/lesion, 8 mg/lesion, 10 mg/lesion, 12 mg/lesion, 15 mg/lesion, 18 mg/lesion, 20 mg/lesion, 22 mg/lesion or another intralesional dose from about 0.2 mg/lesion to about 25 mg/lesion, 30 mg/lesion, 40 mg/lesion, 50 mg/lesion, 75 mg/lesion, 90 mg/lesion, 100 mg/lesion or another total aggregate intralesional dose from about 1 mg/lesion to about 125 mg/lesion per treatment cycle.

In some embodiments, the subject to be treated receives multiple administrations of a nucleotide analogue or nucleotide precursor analogue chemotherapeutic agent within a treatment cycle. In some embodiments, where administration of the chemotherapeutic agent is by systemic, intraperitoneal, or intrapleural administration, the total aggregate dose per treatment cycle for a nucleotide analogue chemotherapeutic agent (e.g., Fluorouracil) ranges from about 0.05 mg/kg to about 25 mg/kg per total aggregate dose per treatment cycle, e.g., 0.075 mg/kg, 0.1 mg/kg, 0.15 mg/kg, 0.2 mg/kg, 0.25 mg/kg, 0.3 mg/kg, 0.35 mg/kg, 0.4 mg/kg, 0.5 mg/kg, 0.6 mg/kg, 0.65 mg/kg, 0.75 mg/kg, 1 mg/kg, 1.1 mg/kg, 1.25 mg/kg, 1.5 mg/kg, 2 mg/kg, 2.5 mg/kg, 3 mg/kg, 4 mg/kg, 5 mg/kg, 8 mg/kg, 10 mg/kg, 12 mg/kg, 15 mg/kg, 18 mg/kg or another dose ranging from about 0.05 mg/kg to about 25 mg/kg per total aggregate dose. In some embodiments, the total aggregate dose per treatment cycle is about 1 mg/kg to about 10 mg/kg per total aggregate dose per treatment cycle.

Dosing Regimes for Non-Nucleotide Analogue Chemotherapeutic Agents

In other embodiments the chemotherapeutic agent to be administered in the combination therapy is a non-nucleotide analogue chemotherapeutic agent. In such e embodiments the dose of a chemotherapeutic agent (e.g., a non-nucleotide analogue chemotherapeutic agent such as Trabectedin), the dose of a recombinant virus, the dose of purified interferon gamma, or both in a combination treatment may be reduced relative to a standard dose accepted in the art for administration of each agent alone. In some embodiments of the treatment methods described herein the reduced dose of the administered chemotherapeutic avoids induction of more than a moderate adverse event in the subject being treated. In some preferred embodiments the dose of chemotherapeutic agent is reduced by about 25% to about 95% relative to a standard dose of the chemotherapeutic agent, e.g., 30%, 35%, 40%, 50%, 60%, 70%, 75%, 80%, 85%, 90%, or another percent dose reduction relative to a standard dose for the cancer to be treated in a range of about 25% to about 95%. In some preferred embodiments the dose is reduced by about 50% to about 85% relative to the a standard dose.

In some embodiments dosing is by a systemic, intraperitoneal, or intrapleural route. Standard dosing by such routes of administration is known for a wide range of non-nucleotide analogue chemotherapeutic agents. In some embodiments systemic, intraperitoneal, or intrapleural dosing ranges from about 0.01 mg/kg to about 50 mg/kg, e.g., 0.03 mg/kg, 0.05 mg/kg, 0.1 mg/kg, 0.5 mg/kg, 1 mg/kg, 1.5 mg/kg, 2 mg/kg, 3 mg/kg, 5 mg/kg, 7 mg/kg, 10 mg/kg, 12 mg/kg, 20 mg/kg, 25 mg/kg, 30 mg/kg, 35 mg/kg, 40 mg/kg, 45 mg/kg, or dose from about 0.01 mg/kg, to about 50 mg/kg. Preferably the dose ranges from about 0.01 mg/kg to about 2 mg/kg.

Intralesional doses range from about 0.01 mg/lesion to about 25 mg/lesion, e.g., 0.05 mg/lesion, 0.1 mg/lesion, 0.5 mg/lesion, 1 mg/lesion, 1.5 mg/lesion, 2 mg/lesion, 3 mg/lesion, 5 mg/lesion, 7 mg/lesion, 10 mg/lesion, 12 mg/lesion, 15 mg/lesion, 20 mg/lesion, or another intralesional dose from about 0.05 mg/lesion to about 25 mg/lesion. Preferably the intralesional dose ranges from about 0.1 mg/lesion to about 10 mg/lesion. The above dosing ranges apply to non-nucleotide analogue chemotherapeutic agents including, but not limited to, topoisomerase inhibitor chemotherapeutic agents (e.g., Doxorubicin, Amsacrine, Etoposide, Etoposide phosphate, Teniposide, Irinotecan, Topotecan, and Camphothecin); SMAC mimetics (e.g., LCL161, GDC-0152, GDC-0917, and SM-406); alkylating agents (e.g., Mechlorethamine, Ifosamide, Uramustine, Carmustine, and Busulfan); PARP inhibitors (e.g., Olaparib); proteasome inhibitors (e.g., Bortezomib, Carfilzomib, NPI-0052, MLN9708, CEP-18770, and ONX0912).

In some preferred embodiments the non-nucleotide analogue chemotherapeutic agent to be administered is Trabectedin. In some preferred embodiments Trabectedin is administered intralesionally at a dose ranging from about 0.0025 mg/lesion to about 0.3 mg/lesion, e.g., 0.005 mg/lesion, 0.0075 mg/lesion, 0.01 mg/lesion, 0.02 mg/lesion, 0.025 mg/lesion, 0.04 mg/lesion, 0.05 mg/lesion, 0.07 mg/lesion, 0.1 mg/lesion, 0.15 mg/lesion, 0.2 mg/lesion, 0.25 mg/lesion, or another intralesional dose from about 0.0025 mg/lesion to about 0.3 mg/lesion. In preferred embodiments intralesional administration of Trabectedin is in a dose ranging from about 0.0025 mg/lesion to about 0.05 mg/lesion.

In some embodiments Trabectedin is administered by a systemic, intraperitoneal, or intrapleural route in a dose of about 0.0025 mg/kg to about 2 mg/kg, e.g., 0.005 mg/kg, 0.0075 mg/kg, 0.01 mg/kg, 0.02 mg/kg, 0.025 mg/kg, 0.04 mg/kg, 0.05 mg/kg, 0.07 mg/kg, 0.1 mg/kg, 0.15 mg/kg, 0.2 mg/kg, 0.3 mg/kg, 0.4 mg/kg, 0.5 mg/kg, 0.7 mg/kg, 0.8 mg/kg, 1 mg/kg, 1.25 mg/kg, 1.5 mg/kg or another dose of Trabectedin from about 0.0025 mg/kg to about 2 mg/kg. In preferred embodiments the administration of Trabectedin is in a dose ranging from about 0.01 mg/kg to about 0.1 mg/kg. In some preferred embodiments the administration of Trabectedin is in a range of about 0.02 mg/kg to about 0.07 mg/kg. In some preferred embodiments Trabectedin is infused intravenously with a dose of about 0.02 mg/kg to about 0.07 mg/kg over a period of about three hours, and with a treatment cycle repeated every three weeks until the end of the treatment.

In some preferred embodiments the non-nucleotide analogue chemotherapeutic agent to be administered is Birinapant. In some preferred embodiments Birinapant is administered intralesionally in a dose ranging from about 0.02 mg/lesion to about 2 mg/lesion, e.g., 0.03 mg/lesion, 0.04 mg/lesion, 0.05 mg/lesion, 0.06 mg/lesion, 0.08 mg/lesion, 0.1 mg/lesion, 0.2 mg/lesion, 0.3 mg/lesion, 0.4 mg/lesion, 0.6 mg/lesion, 0.8 mg/lesion, 1 mg/lesion, 1.2 mg/lesion, 1.5 mg/lesion, 1.8 mg/lesion, or another intralesional dose ranging from about 0.02 mg/lesion to about 2 mg/lesion. In preferred embodiments intralesional administration of Birinapant is in a dose ranging from about 0.02 mg/lesion to about 0.8 mg/lesion.

In other embodiments Birinapant is administered IV in a dose of about 0.02 mg/kg to about 4 mg/kg, e.g., 0.04 mg/kg, 0.06 mg/kg, 0.08 mg/kg, 0.1 mg/kg, 0.2 mg/kg, 0.3 mg/kg, 0.4 mg/kg, 0.6 mg/kg, 0.8 mg/kg, 1 mg/kg, 2 mg/kg, 3 mg/kg, or another dose of Birinapant from about 0.02 mg/kg to about 4 mg/kg. In some preferred embodiments systemic administration of Birinapant is in a dose ranging from about 0.1 mg/kg to about 0.8 mg/kg. In other embodiments the Birinapant is administered by an intraperitoneal or intrapleural route of administration using the same dose range as used for IV administration.

Recombinant Virus Dosing

In some preferred embodiments, administration of a recombinant virus for expression of one or more biotherapeutic agents is by an intralesional route of administration. In some embodiments, the administered intralesional dose of recombinant virus is from about $1 \times 10^7$ infectious particles/lesion to about $1 \times 10^{12}$ infectious particles/lesion, e.g., $2 \times 10^7$, $3 \times 10^7$, $4 \times 10^7$, $5 \times 10^7$, $6 \times 10^7$, $8 \times 10^7$, $1 \times 10^8$, $1.5 \times 10^8$, $2 \times 10^8$, $3 \times 10^8$, $4 \times 10^8$, $6 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $8 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $8 \times 10^{11}$, $9 \times 10^{11}$, or another number of infectious particles/lesion from about $1 \times 10^7$ infectious particles/lesion to about $1 \times 10^{12}$ infectious particles/lesion. In some preferred embodiments, the intralesional viral dose ranges from about $1 \times 10^8$ infectious particles/lesion to about $1 \times 10^{11}$ infectious particles/lesion.

In other embodiments, the recombinant virus expressing one or more biotherapeutic agents is administered by a systemic, intraperitoneal, or intrapleural route. In some embodiments, the systemic, intraperitoneal, or intrapleural dose of recombinant virus is from about $1 \times 10^8$ infectious particles to about $1 \times 10^{13}$ infectious particles per administration, e.g., $2 \times 10^8$, $3 \times 10^8$, $4 \times 10^8$, $5 \times 10^8$, $6 \times 10^8$, $8 \times 10^8$, $1 \times 10^9$, $1.5 \times 10^9$, $2 \times 10^9$, $3 \times 10^9$, $4 \times 10^9$, $6 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, $4 \times 10^{12}$, $5 \times 10^{12}$, $6 \times 10^{12}$, $8 \times 10^{12}$, $9 \times 10^{12}$, or another number of infectious particles per administration from about $1 \times 10^8$ infectious particles to about $1 \times 10^{13}$ infectious particles. In preferred embodiments the dose is about $1 \times 10^9$ to about $1 \times 10^{12}$ infectious particles.

In some embodiments, the subject to be treated is administered multiple doses of a recombinant virus in combination treatment with a chemotherapeutic agent in each treatment cycle.

In other embodiments, where administration of the recombinant virus is intralesional, the total aggregate dose of recombinant viral particles per treatment cycle ranges from about $1 \times 10^8$ infectious particles/lesion to about $1 \times 10^{13}$ infectious particles/lesion, e.g., $2 \times 10^8$, $3 \times 10^8$, $4 \times 10^8$, $5 \times 10^8$, $6 \times 10^8$, $8 \times 10^8$, $1 \times 10^9$, $1.5 \times 10^9$, $2 \times 10^9$, $3 \times 10^9$, $4 \times 10^9$, $6 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $8 \times 10^{11}$, $9 \times 10^{11}$, $1 \times 10^{12}$, $1.5 \times 10^{12}$, $2 \times 10^{12}$, $3 \times 10^{12}$, $4 \times 10^{12}$, $5 \times 10^{12}$, $6 \times 10^{12}$, $8 \times 10^{12}$, $9 \times 10^{12}$ or another number of total infectious particles per treatment cycle from about $1 \times 10^8$ infectious particles/lesion to about $1 \times 10^{13}$ infectious particles/lesion.

In some embodiments, where administration of the recombinant virus is by systemic, intraperitoneal, or intrapleural administration, the total aggregate viral dose per treatment cycle for a recombinant virus is about $1 \times 10^9$ infectious particles to about $1 \times 10^{14}$ infectious particles per treatment cycle, e.g., $2 \times 10^9$, $3 \times 10^9$, $4 \times 10^9$, $5 \times 10^9$, $6 \times 10^9$, $8 \times 10^9$, $1 \times 10^{10}$, $2 \times 10^{10}$, $3 \times 10^{10}$, $4 \times 10^{10}$, $5 \times 10^{10}$, $6 \times 10^{10}$, $8 \times 10^{10}$, $9 \times 10^{10}$, $1 \times 10^{11}$, $1.5 \times 10^{11}$, $2 \times 10^{11}$, $3 \times 10^{11}$, $4 \times 10^{11}$, $6 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $8 \times 10^{13}$, $9 \times 10^{13}$ or another number of total infectious particles per treatment cycle from about $1 \times 10^9$ infectious particles to about $1 \times 10^{14}$ particles.

Caspase Inhibitor Dosing

In some preferred embodiments, a caspase inhibitor is administered intralesionally at a dose ranging from about 0.1 mg/lesion to about 5 mg/lesion, e.g., 0.2 mg/lesion, 0.5 mg/lesion, 1 mg/lesion, 1.5 mg/lesion, 2 mg/lesion, 2.5 mg/lesion, 3 mg/lesion, 3.5 mg/lesion, 4 mg mg/lesion, 4.5 mg/lesion, or another intralesional dose from about 0.1 mg/lesion to about 5 mg/lesion.

In other embodiments, the caspase inhibitor is administered by systemic, intraperitoneal, or intrapleural route of administration. In some embodiments, where the route of administration is systemic, intraperitoneal, or interapleural, the caspase inhibitor dose ranges from about 0.1 mg/kg to about 10 mg/kg, e.g., 0.2 mg/kg, 0.5 mg/kg, 1 mg/kg, 1.5 mg/kg, 2 mg/kg, 3 mg/kg, 4 mg/kg, 5 mg/kg, 6 mg/kg 7.5 mg/kg, 9 mg/kg, or another dose of caspase inhibitor from about 0.1 mg/kg to about 10 mg/kg.

Suitable caspase inhibitors to be used in a treatment method described herein include, but are not limited to, Emricasan, Pralnacasan, VX-799, VX-765, and NCX-1000.

Determination of Specific Dosing

In some embodiments, a subject to be treated is administered a combination treatment as described herein over multiple treatment cycles. The number of treatment cycles may range from 1 to 7, e.g., 2, 3, 4, 5, 6 or another number of treatment cycles from 1 to 7. Where a subject is treated over multiple administration cycles, the total aggregate dose of chemotherapeutic agent, recombinant virus, interferon gamma, or caspase inhibitor per treatment cycle may be varied among different treatment cycles.

In some embodiments, where the subject to be treated is suffering from basal cell carcinoma, the subject a treatment cycle comprises 2-3 administrations in a single week. In other embodiments, where the subject to be treated is suffering from basal cell carcinoma, a treatment cycle comprise 2-3 administrations in two weeks.

In some preferred embodiments, where a human subject is to be treated for a cancer amenable to intralesional administration (e.g., basal cell carcinoma), both 5-FU and the recombinant virus are administered by an intralesional route. In exemplary preferred embodiments the recombinant virus is a (non-replicative) adenovirus for expression of interferon gamma administered in a dose ranging from about $5 \times 10^{10}$ viral particles/lesion to about $3 \times 10^{11}$ viral particles/lesion in combination with Fluorouracil in a dose ranging from about 1 mg/lesion to about 25 mg/lesion. The just-mentioned combination treatment is repeated once a week for up to four weeks.

In a case where a subject's status does improve, upon reliable medical advice, doses being administered may be temporarily reduced or temporarily suspended for a certain length of time (e.g., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, or 60 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

The person of ordinary skill in the art will appreciate that a suitable therapeutically effective dose of a chemotherapeutic agent in combination with a recombinant virus, interferon gamma, and/or a caspase inhibitor, as described herein, will depend upon factors such as the particular chemotherapeutic agent, the cancer stage, the characteristics of the subject or host in need of treatment (e.g., weight), and the properties of the particular type of cancer to be treated, but can nevertheless be determined in a manner known in the art according to the particular circumstances surrounding the case, including, e.g., the specific chemotherapeutic agent being administered, the route of administration, the cancer being treated, and the subject being treated. The desired dose may conveniently be presented in a single dose or as divided doses administered simultaneously (or over a short period of time) or at appropriate intervals, for example as two, three, four or more sub-doses per day.

Such dosages may be altered depending on a number of variables, not limited to the activity and toxicity of the chemotherapeutic agent, the recombinant virus, and/or a caspase inhibitor to be used, the type of cancer to be treated, the mode of administration, the requirements of the individual subject, the stage of cancer being treated, and the judgment of the practitioner.

According to the methods described herein, a chemotherapeutic agent is administered in combination with other agents (e.g., at least a recombinant virus, interferon gamma, and/or a caspase inhibitor) for treatment of a cancer to achieve a synergistic therapeutic effect. In general, agents being administered in combination do not necessarily have to be administered in the same pharmaceutical composition, and may, because of different physical and chemical characteristics, preferably be administered by different routes.

A chemotherapeutic agent and any of a recombinant, a caspase inhibitor, and/or purified interferon gamma may be administered concurrently (e.g., simultaneously, essentially simultaneously or within the same treatment protocol) or sequentially, depending upon the nature and stage of the cancer, the condition of the patient, and the actual choice of therapeutic agents used.

It is known to those of skill in the art that therapeutically-effective dosages can vary when the therapeutic agents (e.g., a chemotherapeutic agent and a recombinant virus) are used in treatment combinations.

It will be understood by those skilled in the art that the dosage regimen to treat the cancer for which relief is sought, can be modified in accordance with a variety of factors. These factors include the specific combination of therapeutic agents being used, the cancer type and stage from which the subject suffers, as well as the age, weight, sex, diet, and medical condition of the subject.

The chemotherapeutic agent and additional therapeutic agents (e.g., a recombinant virus, a caspase inhibitor, and/or interferon gamma) which make up a combination therapy disclosed herein may be administered as a combined pharmaceutical composition as described herein, or in separate dosage forms intended for substantially simultaneous administration by the same or separate routes of administration. The therapeutic agents that make up the combination therapy may also be administered sequentially, with either therapeutic agent being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of various physiological parameters may also be evaluated to determine the optimal dose interval.

Initial administration can be via any route practical, such as, for example, an intravenous injection, a bolus injection, infusion over 5 minutes to about 5 hours, a pill, a capsule, injection, topical application, transdermal patch, and the like, or combination thereof. In some preferred embodiments, administration is by intralesional injection.

The combinations of chemotherapeutic agents, recombinant viruses, caspase inhibitors, and/or purified interferon gamma of the methods described herein can be used in the preparation of medicaments for the treatment of a subject suffering from a cancer according to any of the methods described herein.

Combination Pharmaceutical Compositions

Described herein are combination pharmaceutical compositions, for use in the treatment of a cancer, comprising therapeutically effective amounts of a nucleotide analogue or nucleotide precursor analogue chemotherapeutic agent in combination with at least one of: (i) a recombinant virus for expression of one or more biotherapeutic agents in a human subject as described herein; (ii) a caspase inhibitor; and (iii) interferon gamma.

In some preferred embodiments, the nucleotide analogue chemotherapeutic agent in the combination pharmaceutical composition is Fluorouracil.

Also described herein are combination pharmaceutical compositions, for use in the treatment of a cancer, comprising therapeutically effective amounts of: (i) a chemotherapeutic agent other than a nucleotide analogue or nucleotide precursor analogue chemotherapeutic agent in combination with at least one of: (i) a recombinant virus for expression of one or more biotherapeutic agents in a human subject as described herein; (ii) a caspase inhibitor; and (iii) purified interferon gamma.

In some embodiments the non-nucleotide chemotherapeutic agent to be included in the combination pharmaceutical composition is of a class selected from among DNA-binding agents, second mitochondrial-derived activator of caspases (SMAC) mimetics, alkylating agents, topoisomerase inhibitors, nucleoside analogs, proteasome inhibitors, and poly ADP ribose polymerase (PARP) inhibitors. In some preferred embodiments the chemotherapeutic agent to be included in the combination pharmaceutical composition is Trabectedin or Birinapant.

In some preferred embodiments, the recombinant virus for use in the above-mentioned combination pharmaceutical compositions is a recombinant adenovirus for expression of interferon gamma.

Controlled Release Combination Pharmaceutical Compositions

Also provided herein are controlled release pharmaceutical compositions. Controlled release refers to the release of therapeutic agents from a dosage form in which they are incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of a therapeutic agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments controlled release pharmaceutical compositions include: (i) a recombinant expression virus for expression of one or more cytokines in a human subject; and (ii) a controlled release $SiO_2$ matrix gel.

In other embodiments the controlled release pharmaceutical compositions provided herein include (i) a controlled-release matrix; (ii) a caspase inhibitor dispersed within the controlled-release matrix; and a chemotherapeutic agent, as described herein, dispersed within the controlled release matrix; and (iii) a chemotherapeutic agent, as described herein, dispersed within the controlled release matrix. Optionally, a controlled release pharmaceutical formulation containing a caspase inhibitor and a chemotherapeutic agent further includes a recombinant virus for expression of one or more biotherapeutic agents in a human subject as described herein.

In other embodiments controlled release pharmaceutical compositions include: (i) a controlled-release matrix; (ii) a recombinant virus dispersed within the controlled-release matrix; and (iii) a chemotherapeutic agent, as described herein, dispersed within the controlled release matrix.

Also provided herein are controlled release pharmaceutical compositions that include: (i) a controlled-release matrix; (ii) purified interferon gamma dispersed within the controlled-release matrix; and (iii) a chemotherapeutic agent, as described herein, dispersed within the controlled release matrix.

The controlled release pharmaceutical compositions provided herein allow the release profile of an active agent within the combination formulation to be customised so that release of one or more of these active agents occurs over a preferred time interval. In some preferred embodiments, the chemotherapeutic agent in the controlled release pharmaceutical composition is a nucleotide analogue chemotherapeutic agent, e.g., Fluorouracil.

In other embodiments the chemotherapeutic agent in the controlled release pharmaceutical composition is a non-nucleotide analogue chemotherapeutic agent, e.g., Trabectedin or Birinapant. In other embodiments the chemotherapeutic agent is Trabectedin.

In some embodiments the pharmaceutical composition comprises from about 0.7 mg to about 340 mg of a nucleotide analogue chemotherapeutic agent, e.g., 1 mg, 3 mg, 5 mg, 10 mg, 20 mg, 40 mg, 60 mg, 80 mg, 100 mg, 120 mg, 150 mg, 280 mg, 200 mg, 250 mg, 270 mg, or another dose from about 0.7 mg to about 340 mg of the chemotherapeutic agent. In some embodiments the controlled release pharmaceutical composition comprises from about 5 mg to about 200 mg of the nucleotide analogue chemotherapeutic agent. In other embodiments the controlled release pharmaceutical composition comprises from about 25 mg to about 150 mg of the nucleotide analogue chemotherapeutic agent.

In some embodiments, one or more of the active agents is released over a time period ranging from about one hour to about five weeks, e.g., 2 hours, 3 hours, 4 hours, 6 hours, 8 hours, 12 hours, 18 hours, 24 hours, 2 days, 3 days, 5 days, 1 week, 10 days, 2 weeks, 18 days, 3 weeks, 4 weeks, or another period from about one hour to about five weeks.

In some embodiments, the controlled release profile has a release rate higher at the beginning of the release period following administration, and then decreases over time (first order release kinetics). In other embodiments, the release rate progressively increases over the release period following administration. In preferred embodiments, the release profile remains relatively constant over the entire release period following administration until all of the active agent is released (zero order release kinetics).

In preferred embodiments the release profile of the chemotherapeutic agent upon administration of the controlled release pharmaceutical composition is adapted to avoid induction of more than a moderate adverse event in the human subject. In some embodiments, the release rate of the chemotherapeutic agent is about 0.5% of the total dose/day to about 10% of the total dose per day, e.g., 0.6%, 0.8%, 1%, 1.1%, 1.2%, 1.5%, 1.8%, 2%, 2.5%, 2.75%, 3%, 3.5%, 4%, 6%, 7%, 8%, 9% or another percentage of the total dose per day from about 0.5% to about 10% per day.

In some embodiments, the rate of release (as a percentage of total dose) of a chemotherapeutic agent in the controlled release formulation is distinct from that the release profile of another active agent in the formulation (e.g., a recombinant virus and/or a caspase inhibitor).

In some embodiments, of any of the above-mentioned pharmaceutical compositions, the chemotherapeutic agent is a nucleotide analogue or nucleotide precursor analogue chemotherapeutic agent as described herein. In preferred embodiments the nucleotide analogue chemotherapeutic agent is Fluorouracil.

In other embodiments, of any of the above-mentioned pharmaceutical compositions, the chemotherapeutic agent is a chemotherapeutic agent other than a nucleotide analogue or nucleotide precursor analogue chemotherapeutic agent. In some embodiments, the chemotherapeutic agent in a combination pharmaceutical composition described above is of a class selected from among: DNA-binding agents, second mitochondrial-derived activator of caspases (SMAC) mimetics, alkylating agents, topoisomerase inhibitors, proteasome inhibitors, and poly ADP ribose polymerase (PARP) inhibitors. In some preferred embodiments, the chemotherapeutic agent is Trabectedin or Birinapant.

In some embodiments, where the controlled release pharmaceutical composition includes interferon gamma, the interferon gamma is released at a rate of about 1 µg/day to about 10 µg/day for systemic delivery, e.g., 2 µg/day, 3 µg/day, 4 µg/day, 5 µg/day, 7 µg/day, 8 µg/day, or another release rate for systemic administration of purified interferon gamma ranging from about 1 µg/day to about 10 µg/day.

In some embodiments, where the controlled release pharmaceutical composition includes interferon gamma, the interferon gamma is released at a rate of about 5 ng/day to about 200 ng/day for localized delivery, e.g., implantation within a tumour, e.g., 10 ng/day, 20 ng/day, 30 ng/day, 50 ng/day, 75 ng/day, 100 ng/day, 125 ng/day, 150 ng/day, 175 ng/day, or another release rate for local administration ranging from about 10 ng/day to about 200 ng/day.

Suitable controlled release matrices for controlled release pharmaceutical compositions have been described in art. In some embodiments, the controlled release matrix comprises a bioresorbable sol-gel derived alkoxysilane $Si(OR)_4$ matrix gel ("$SiO_2$ matrix gel") for sustained delivery of active therapeutic agents including small molecule drugs and recombinant viruses as described in international patent application publications WO2005082781 entitled "Method for Preparing Adjustably Bioresorbable Sol-Gel Derived $SiO_2$," and WO2007135224 entitled "Method for Storing Silica-Based Material, Package Produced with the Method, and Use of Package for Packaging of Silica-Based Products." This technology has been commercialised by DelSiTech Ltd (Turku, Finland).

In brief, the $SiO_2$ matrix gel sol-gel is prepared by the sol-gel process wherein the $SiO_2$ matrix gel is prepared from a sol comprising $SiO_2$ that has turned to a gel. Sol-gel derived $SiO_2$ is typically prepared from alkoxides or inorganic silicates that via hydrolysis form a sol that contains either partly hydrolysed silica species or fully hydrolysed silicic acid. Consequent condensation reactions of SiOH containing species lead to formation of larger silica species with increasing amount of siloxane bonds. Furthermore, the species aggregate, form nanosized particles and/or larger aggregates until a gel is formed. In the form of a gel, the solid state dominates, but the system still contains varying amounts of liquids and the material is typically soft and viscoelastic before drying and hard and brittle if it is extensively dried. In the form of a sol, liquid state dominates, but the system contains varying amounts of solid phase(s) and the material is still flowable. The time from when the $SiO_2$ sol is prepared until the sol turns to a gel is referred to as sol ageing time. Spontaneous drying typically occurs when the sol is aged so that the system allows evaporation in ambient conditions. Generation of the controlled release pharmaceutical composition is achieved by adding to the sol, before gel formation, the desired amounts of (i) the chemotherapeutic agent and (ii) at least one of a recombinant virus for expression of a biotherapeutic agent; a caspase inhibitor; and/or purified interferon gamma.

Release rates of the active agents in $SiO_2$ gel-based controlled release pharmaceutical compositions can be adjusted as needed. Generally the maximum dissolution rate of the $SiO_2$ gel matrix and release rate of the active agents occurs for $SiO_2$ gels having a molar ratio of water to alkoxide of about 2, with ratios lower or higher than this resulting in slower dissolution and release rates. Further, It should also be noted that large amounts of active agent comprised within the $SiO_2$ gel matrix increases dissolution of the matrix and the release rate(s) of the active agents. The controlled release pharmaceutical compositions can be prepared as nano- and microspheres mainly for oral, parenteral, pulmonary, topical, transdermal and surgically implantable administration.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, any of the above-mentioned pharmaceutical compositions further include an immune response-inducing or enhancing agent as described herein (e.g., a purified chemokine, a purified polarising cytokine, or a TLR agonist).

Formulation of Therapeutic Agents

Any of the therapeutic agents described herein can be formulated either alone or in combined pharmaceutical compositions as described herein for administration to a subject via any conventional means including, but not limited to, intralesional, parenteral (e.g., intravenous, subcutaneous, intramuscular, intraperitoneal, or intrapleural), oral, or transdermal administration routes.

Therapeutic agents can be formulated into any suitable dosage form, including but not limited to, injectable formulations, aqueous oral dispersions, liquids, mists, gels, syrups, elixirs, slurries, suspensions and the like, for oral ingestion by a patient to be treated, solid oral dosage forms, controlled release formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the therapeutic agents described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical solid dosage forms can include, in addition to the therapeutic agents, one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the therapeutic agents from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel® PH101, Avicel®PH102, Avicel®PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, PolyplasdoneXL-10, and Povidone®K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

Liquid formulation dosage forms for oral administration can be aqueous suspensions selected from the group including, but not limited to, pharmaceutically acceptable aqueous oral dispersions, emulsions, solutions, elixirs, gels, and syrups.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Injectable Formulations

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, therapeutic agents described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the therapeutic agents in water-soluble form. Additionally, suspensions of the therapeutic agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of a therapeutic agent to allow for the preparation of highly concentrated solutions. Alternatively, the therapeutic agent may be in powder form for constitution with a suitable vehicle, e.g., sterile pyrogen-free water, before use. The therapeutic agents described herein may be in unit dosage forms suitable for single administration of precise dosages. In unit dosage form, the formulation is divided into unit doses containing appropriate quantities of one or more therapeutic agents. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

EXAMPLES

Example 1—Synergistic Induction of HeLa (RIP3$^-$) or HeLa (RIP3$^+$) Cell Death by Fluorouracil in Combination with Purified Interferon Gamma (IFN Gamma)-Expressing Adenovirus (ASN-002) in Vitro Materials and Methods
Cell Death Kinetics in Response to ASN-002 Adenovirus Transduction
HeLa-RIP3$^-$ or HeLa-RIP3$^+$ cells were plated in six-well plates and allowed to adhere for 24 hours before infection. Cells were infected with various multiplicities of infection (MOI) of ASN-002, a replication-deficient adenovirus for expression of IFN gamma. Cells were transduced with the virus in serum-free media for 2 hours. Complete DMEM media was then added and cells were evaluated over the period of 5 days.
Dose Response for Fluorouracil
HeLa-RIP3$^-$ or HeLa-RIP3$^+$ cells (250,000/well) were seeded in six-well plates in complete DMEM medium, and after 24 hours, cells were treated with multiple doses of Fluorouracil. Cell viability was determined 48 hours post treatment via trypan blue exclusion analysis.
Cell Death Kinetics in Response to Combination of Fluorouracil Plus ASN-002 Adenovirus Transduction
HeLa-RIP3$^-$ cells (250,000/well) cells were plated in six-well plates 24 hours prior to infection. ASN-002 infections were performed in serum-free medium at multiplicities of infection (MOI) of 10. Two doses of Fluorouracil were co-administered with viruses, and cell death kinetics was analyzed over the period of 3 days.
Induction of Cell Death by TNF Alpha in HeLa-RIP3$^-$ or HeLa-RIP3$^+$ Cells in the Presence of a Pan Caspase Inhibitor
HeLa-RIP3 cells (250,000/well) were plated in six-well plates 24 hours prior to treatment with TNF alpha and cycloheximide (TCZ treatment). Cells were pre-treated with CHX (250 ng/ml) and the pan caspase inhibitor zVAD (50 µM) one hour before TNF alpha (50 ng/ml) treatment. Cell viability was determined after 12-15 hours by trypan blue exclusion analysis.
Results
Cell Death Kinetics in Response to ASN-002 Adenovirus Transduction
As shown in FIG. 1 transduction of HeLa-RIP3$^-$ ("HeLa") or HeLa-RIP3$^+$ ("HeLa-RIP") cells with ASN-002 at multiplicities of infection of 10, 100, and 1000 led to progressively faster cell death over a period of five days with a $T_{1/2}$ of approximately 4 days, 3 days, and 2.5 days respectively. The time course of cell death was generally similar between HeLa-RIP3$^-$ and HeLa-RIP3$^+$ cells, although, the time course appeared to be slightly faster in HeLa RIP-3$^+$ cells for an MOI of 10 or 100.
Dose Response for Fluorouracil
Dose response curves were determined for the nucleotide analogue chemotherapeutic Fluorouracil (FIG. 2). The $ED_{50}$ at 48 hours was approximately 50 µM.
Induction of Cell Death by TNF Alpha is RIPS-Dependent and Apoptosis-Independent in HeLa cells.
As shown in FIG. 3, TNF alpha failed to induce cell death in HeLa (RIP3$^-$) cells under any condition. In contrast, TNF alpha induced a high level of cell death (about 70%) even the presence of inhibitors of apoptosis (cycloheximide plus zVAD) relative to untreated cells. These data suggest that TNF alpha induces cell death primarily, if not exclusively, by a RIP3-dependent pathway, likely to be necroptosis.
Synergistic Induction of Cell Death in HeLa(RIP3$^-$) Cells with a Combination of Fluorouracil and ASN-002.
As shown in FIG. 4, a combination of Fluorouracil with transduction with an IFN gamma expression adenoviral vector (ASN-002) induces a level of cell death that is significantly higher than what would be expected based on merely the sum of cell death percentages induced by these individual agents (chemotherapeutic or ASN-002) alone. This indicates synergy between Fluorouracil and IFN gamma expression in inducing cancer cell death.

Example 2—Induction of Cell Death by Fluorouracil, ASN-002, Fluorouracil Plus ASN-002, Fluorouracil Plus Purified IFN Gamma in the Presence of Inhibitors of Apoptosis and Necroptosis in RIP3$^+$ and RIP3$^-$ HeLa Cells In order to understand which of several possible cell death pathways are activated by Fluorouracil or ASN-002 treatment alone and in combination, experiments were carried out with these agents in the presence of inhibitors of apoptosis and/or necroptosis in HeLa (RIP3$^+$/necroptosis-competent) cells.

As shown in FIG. 5A, 10 µM Fluorouracil (plus the negative control AdCMV-NULL virus) induced approximately 35% cell death in HeLa-RIP3$^+$ cells. Strikingly, in the presence of the pan caspase inhibitor zVAD (50 µM) Fluorouracil induced greatly increased cell death, relative to treatment with Fluorouracil alone, of about 80%. Fluorouracil in the presence of the necroptosis inhibitor Necrosulfonamide (1 µM) induced a level of cell death only slightly greater than that observed with Fluorouracil alone (45% vs 35%). Fluorouracil in the presence of inhibitors of both apoptosis (zVAD) and necroptosis (NSA) induced a level of cell death similar to that of Fluorouracil alone.

As shown in FIG. 5B, treatment with a combination of Fluorouracil plus ASN-002 induced synergistic cell death of approximately 90%, which was increased to about 97% in the presence of zVAD. NSA did not significantly alter cell death induced by the combination alone. In contrast, in the presence of inhibitors of both apoptosis (zVAD) and necroptosis (NSA), Fluorouracil plus ASN-002 had a greatly diminished, albeit substantial, level of cell death of about 37% similar to that observed with Fluorouracil alone.

Treatment with ASN-002 alone (FIG. 6B) or purified IFN gamma alone (FIG. 6C) induced approximately 25% and 30% cell death respectively. As observed for Fluorouracil alone, treatment with ASN-002 alone in the presence of zVAD greatly enhanced ASN-002-induced cell death to a level of about 60%, while treatment with ASN alone in the presence of NSA induced the same level of cell death observed with no treatment other than with ASN-002. Treatment with ASN-002 in the presence of both zVAD and NSA, unlike treatment with ASN-002 in the presence of zVAD only, resulted in a level of cell death no greater than that caused by ASN alone.

In follow-up experiments, RIP3$^-$ (necroptosis-deficient) HeLa cells were subjected to the same treatments as described above. As shown in FIGS. 7A and 7B, Fluorouracil treatment, alone or in combination with AdCMV, induced a level of cell death in RIP3$^-$ HeLa cells similar to that observed in RIP3$^+$ HeLa cells in response to the same treatment. However, treatment with Fluorouracil in the presence of zVAD in RIP3$^-$ HeLa cells not only failed to increase cell death relative to that induced by Fluorouracil alone (or Fluorouracil plus AdCMV), but was slightly lower. Treatment of RIP3$^-$ HeLa cells with ASN-002 alone (FIG. 8B) or purified IFN gamma alone (FIG. 8C) induced approximately 35% and 30% cell death, respectively. Treatment with these agents in the presence of zVAD resulted in a marked, though not complete, rescue of cell death.

Treatment of RIP3$^-$ HeLa cells with a combination of Fluorouracil plus ASN-002 (FIG. 7C) or Fluorouracil plus purified IFN gamma (FIG. 7D) also induced a synergistic level of cell death of about 83% and 73% respectively. However, in the presence of zVAD the combination treatments were reduced to cell death levels of 68% and 55%, respectively.

These results suggest that in the presence of the inhibition of inhibitors of apoptosis (e.g., zVAD), combination treatment-induced cell death is "shunted" at least in part to necroptosis, as evidenced by the fact that (1) in RIP3$^+$ cell death is greatly reduced in the presence of both zVAD and NSA, but not NSA on its own; and (2) zVAD fails to enhance cell death in RIP3$^-$ (necroptosis-deficient) HeLa cells. Interestingly, even under conditions where both apoptosis and necroptosis cell death pathways are inhibited, residual cell death is still observed suggesting a role for an apoptosis and necroptosis-independent cell death pathway where both apoptosis and necroptosis is inhibited. Alternatively, this may reflect failure of the inhibitors to completely inhibit apoptotic and necroptotic cell death pathways. As a number of cancers are known to be deficient in apoptosis or necroptosis cell death pathways, the ability of Fluorouracil in combination with IFN gamma to induce cell death in cells deficient in either or indeed both of these cell death pathways suggests that this treatment is likely to be highly effective against a broad range of cancers, and particularly those that are refractory or resistant to conventional chemotherapeutic approaches.

Example 3—Synergistic Induction of HeLa (RIP3$^-$) or HeLa (RIP3$^+$) Cell Death by Chemotherapeutic Agents in Combination with an Adenovirus-Expressing Interferon Gamma (ASN-002) In Vitro Materials and Methods
Cell Death Kinetics in Response to ASN-002 Adenovirus Transduction HeLa-RIP3$^-$ or HeLa-RIP3$^+$ cells were plated in six-well plates and allowed to adhere for 24 hours before infection. Cells were infected with various multiplicities of infection (MOI) of ASN-002, a replication-deficient adenovirus for expression of IFN gamma. Cells were transduced with the virus in serum-free media for 2 hours. Complete DMEM media was then added and cells were evaluated over the period of 5 days.
Dose Response for Chemotherapeutic Agents HeLa-RIP3$^-$ or HeLa-RIP3$^+$ cells (250,000/well) were seeded in six-well plates in complete DMEM medium, and after 24 hours, cells were treated with multiple doses of the Trabectedin, Birinapant, or Cisplatin. Cell viability was determined 48 hours post treatment via trypan blue exclusion analysis.
Cell Death Kinetics in Response to Combination of a Chemotherapeutic Agent Plus ASN-002 Adenovirus Transduction HeLa-RIP3$^-$ cells (250,000/well) cells were plated in six-well plates 24 hours prior to infection. ASN-002 infections were performed in serum-free medium at multiplicities of infection (MOI) of 10. Two doses of chemotherapeutic agents were co-administered with viruses, and cell death kinetics was analyzed over the period of 3 days.
Induction of Cell Death by TNF Alpha in HeLa-RIP3$^-$ or HeLa-RIP3$^+$ Cells in the Presence of a Pan Caspase Inhibitor HeLa-RIP3 cells (250,000/well) were plated in six-well plates 24 hours prior to treatment with TNF alpha and cycloheximide (TCZ treatment). Cells were pre-treated with CHX (250 ng/ml) and the pan caspase inhibitor zVAD (50 µM) one hour before TNF alpha (50 ng/ml) treatment. Cell viability was determined after 12-15 hours by trypan blue exclusion analysis.
Results
Cell Death Kinetics in Response to ASN-002 Adenovirus Transduction As shown in FIG. 1 transduction of HeLa-RIP3$^-$ ("HeLa") or HeLa-RIP3$^+$ ("HeLa-RIP") cells with ASN-002 at multiplicities of infection of 10, 100, and 1000 led to progressively faster cell death over a period of five days with a $T_{1/2}$ of approximately 4 days, 3 days, and 2.5 days respectively. The time course of cell death was generally similar between HeLa-RIP3$^-$ and HeLa-RIP3$^+$ cells, although, the time course appeared to be slightly faster in HeLa RIP-3+ cells for an MOI of 10 or 100.

Dose Response

Dose response curves were determined for Birinapant (FIG. 9), Trabectedin (FIG. 10), and Cisplatin (FIG. 11) in HeLa-RIP3− ("HeLa") and HeLa-RIP3+ ("HeLa-RIP") cells. The $ED_{50}$ at 48 hours were approximately 30 µM (Birinapant), 10 nM (Trabectedin), and 10 µg/ml (Cisplatin).

Induction of Cell Death by TNF Alpha is RIP3-Dependent and Apoptosis-Independent in HeLa cells.

As shown in FIG. 12, TNF alpha failed to induce cell death in HeLa (RIP3−) cells under any condition. In contrast, TNF alpha induced a high level of cell death (about 70%) even the presence of inhibitors of apoptosis (cycloheximide plus zVAD) relative to untreated cells. These data suggest that TNF alpha induces cell death primarily, if not exclusively, by a RIP3-dependent pathway, likely to be necroptosis.

Synergistic Induction of Cell Death in HeLa(RIP3−) Cells with a Combination of Birinapant and ASN-002 or Trabectedin and ASN-002.

As shown in FIG. 13 (Birinapant) and FIG. 14 (Trabectedin), a combination of any one of these chemotherapeutic agents with transduction with an IFN expression adenoviral vector (ASN-002) induces a level of cell death that is significantly higher than what would be expected based on merely the sum of cell death percentages induced by these individual agents (chemotherapeutic or ASN-002) alone. This suggests synergy between these reagents in inducing cancer cell death. These results were in contrast to those obtained with a combination of Cisplatin plus ASN-002 (FIG. 15), which, in fact, induced approximately the same level of cell death as that induced by Cisplatin alone at the same concentration (15 µg/ml).

Example 4—Chemo-Viral Combination Treatment Synergy Depends on IFN Gamma Expression In order to determine whether the synergistic cell death observed in HeLA (RIP3−) cells was dependent on expression of IFN gamma (the "payload") following transduction with ASN-002, experiments were conducted using Ad-CMV NULL (vector only) adenovirus (negative control) as well as exogenous IFN gamma (positive control) each in combination with Birinapant.

As shown in FIG. 16 Birinapant in combination with the Ad-CMV-NULL virus (FIG. 16A) induced a level of cell death indistinguishable from that induced by Birinapant alone at the same concentration. Consistent with this finding, the Ad-CMV-NULL virus alone failed to induce significant cell death (FIG. 16B). Importantly, as shown in FIG. 16C, purified IFN gamma in combination with Birinapant induced a synergistic level of cell death similar to that observed with the combination of ASN-002 plus Birinapant. These results indicate that synergistic cell death observed with ASN-002 plus Birinapant is dependent on the expression of IFN gamma and not on the presence of adenovirus per se.

Example 5—Induction of Cell Death by Trabectedin and Trabectedin Plus ASN-002, or IFN Gamma in the Presence of Inhibitors of Apoptosis and Necroptosis in RIP3+ and RIP3− HeLa Cells In order to understand which of several possible cell death pathways are activated by Trabectedin treatment alone and in combination with IFN gamma (virus expressed or exogenously added), experiments were carried out with these agents, alone or in combination, in the presence of inhibitors of apoptosis and/or necroptosis inhibitors in both HeLa (RIP3+/necroptosis-competent) cells and HeLa (RIP3−/necroptosis-deficient) cells.

As shown in FIGS. 19A and 19C, 2.5 nM Trabectedin (plus the negative control AdCMV-NULL virus or alone) induced approximately 35% cell death in HeLa-RIP3+ cells. In the presence of the pan caspase inhibitor zVAD, Trabectedin induced dramatically increased cell death, relative to treatment with Trabectedin alone, of about 95% (FIG. 19C). Trabectedin in the presence of the necroptosis inhibitor NSA induced a level of cell death slightly lower that observed with Trabectedin treatment alone (FIG. 19C). Trabectedin in the presence of inhibitors of both apoptosis (zVAD) and necroptosis (NSA) induced a level of cell of about 60%, which was intermediate to the level of cell death resulting from treatment with Trabectedin alone and Trabectedin plus zVAD suggesting that under these conditions Trabectedin can induce substantial cell death through pathway other than apoptosis or necroptosis.

Figure 17C:
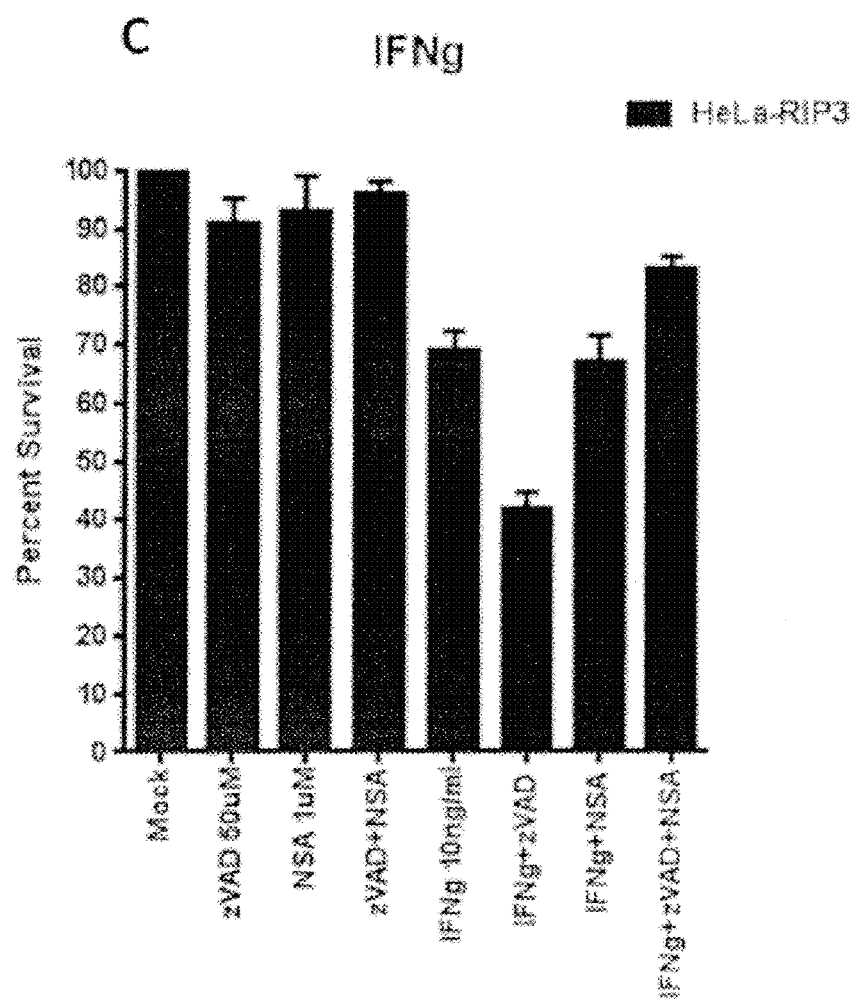
Figure 18C:
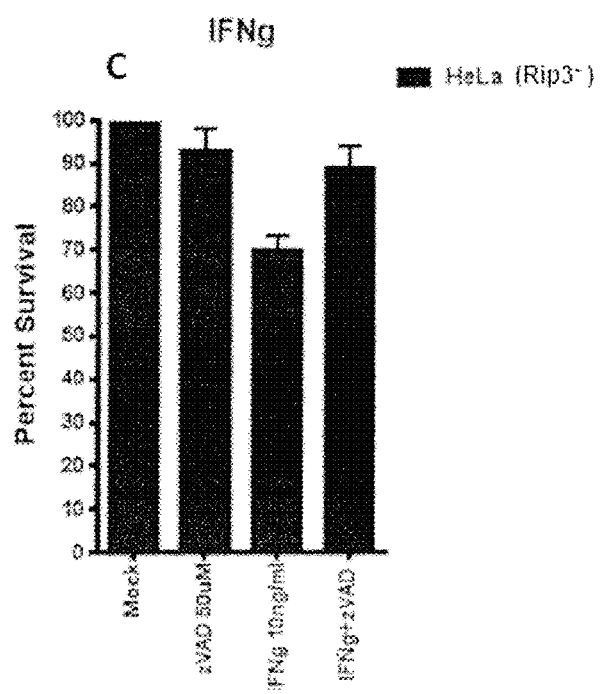

Similar results were observed for ASN002 alone in RIP+ HeLa cells (FIG. 17B) and purified IFN gamma alone (FIG. 17C) with no cell death observed for control virus (FIG. 17A). In RIP− HeLa cells ASN002 in the presence of ZVAD (FIG. 18B) showed significantly reduced cell death, as did IFN gamma alone in the presence of ZVAD in RIP3− cells (FIG. 18C), with no cell death observed under any condition with the control AdCMV virus (FIG. 18A).

As shown in FIG. 19B, treatment with a combination of Trabectedin plus ASN-002 induced synergistic cell death of approximately 80%, which was increased to about 97% in the presence of zVAD. NSA did not significantly alter cell death induced by the combination treatment. The combination of Trabectedin plus ASN-002, in the presence of inhibitors of both apoptosis (zVAD) and necroptosis (NSA) (FIG. 19B), induced a level of cell death of about 80% similar to that observed with the combination treatment alone, but lower than that observed in the presence of only the zVAD apoptotic inhibitor. A similar pattern was observed with the combination of Trabectedin plus purified IFN gamma (FIG. 19D) although this combination resulted in somewhat lower cell death than the combination of Trabectedin plus ASN-002.

The same treatment regimens were tested in RIP3− (necroptosis-deficient) HeLa cells. Trabectedin alone (FIG. 20A) or plus AdCMV-NULL (FIG. 20B) induced a level of cell death in RIP3− HeLa cells (33%) similar to that observed in RIP3+ HeLa cells. Surprisingly, cell death in RIP3− HeLa cells following treatment with Trabectedin alone (FIG. 20A) or plus AdCMV-NULL (FIG. 20B) was greatly increased in the presence of zVAD (87% cell death) relative to treatment with Trabectedin alone despite inhibition of apoptosis and necroptosis deficiency suggesting that, under these conditions, Trabectedin effectively engages a cell death pathway other than apoptosis or necroptosis.

As shown in FIG. 20C, treatment with a combination of Trabectedin plus ASN-002 induced synergistic cell death of approximately 77% similar to that observed in RIP3+-HeLa cells, which was increased to about 88% in the presence of zVAD (FIG. 20C), a level similar to that observed with treatment of Trabectedin alone in the presence of zVAD. Likewise Trabectedin in combination with purified IFN-gamma gave similar results (FIG. 20D).

These data strongly suggest that under conditions where either apoptosis, necroptosis, or both are blocked, Trabectedin alone or in combination induces a high level of cell death through a cell death pathway other than apoptosis or necroptosis (e.g., parthanatos or autophagic cell death). Thus, the efficacy of Trabectedin (alone or in combination therapies) against cancer cells is likely not only to be retained against cancer cells with defective apoptosis, but may actually be enhanced. Indeed, this conclusion is also likely to hold for Trabectedin treatment of cancers that are defective in both apoptotic and necroptotic cell death pathways.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2016902922 and AU 2016902923 filed 25 Jul. 2016, the entire contents of which are incorporated herein by reference.

REFERENCES

Aachoui et al. (2013) Science 339, 975-978.
Adeno-Associated Virus: Methods and Protocols, Methods in Mol. Biol, Snyder and Moullier (eds) (2011).
Amer et al (2014) Molecular and Cellular Therapies 2, 27.
Bonilla et al (2016), Nature Genetics 48(4):398-406.
Bucholz et al (2015) Trends in Biotechnology 33(12), 777-790.
Cattaneo (2010) PLoS Pathogens 6(6), e10010973.
Chang et al (2010) Journal of Urology 183(4), 1611-1618.
Chodorge et al (2012) Cell Death & Differentiation 19(7), 1187-1195.
Cody et al (2013) Journal of Genetic Syndromes & Gene Therapy 4(1), 126.
Cook et al (2014) Cell Death and Differentiation 21, 1600-1612.
Ebert et al (2007) Nature Methods 4, 721-726.
Emeagi et al (2013) Current Molecular Medicine 13(4), 602-625.
Finke et al (2005) Current Topics in Microbiology and Immunology 292, 165-200.
Fukizawa et al (2010) International J of Mol. Med 25(1), 3-10.
Gawad et al (2016) Nature Reviews Genetics 17, 175-188.
Gene Therapy Protocols, Methods in Mol. Biol., Vol. 2 Joseph LeDoux (ed.), 2008.
Gene Therapy Protocols, Methods in Mol. Biol., Vol. 1 Joseph LeDoux (ed.), 2008.
Guo et al (2002), Blood 99, 3419-3426.
Herpes Simplex Virus: Methods and Protocols, Methods in Mol. Biol., Diefenbach and Fraefel (eds), 2014.
Hoang-Le et al (2009), Gene Therapy 16, 190-199.
Lawrence et al (2014), Nature 505(7484):495-501.
Lundstrom (2015) Viruses 7(5), 2321-2333.
Martinez-Sales (1999) Current Opinion in Biotechnology 10, 458-464.
Merten et al (2016) Molecular Therapy—Methods & Clinical Development 3, 16017.
Morizono et al (2005) Nature Medicine 11, 346-352.
Munch et al (2011) Molecular Therapy 19, 686-693.
Munch et al (2013) Molecular Therapy 21, 109-118.
Navin et al (2014) Genome Biology 15, 452.
Orozco et al (2014) Cell Death and Differentiation 21, 1511-1521.
Quetglas et al (2010) Virus Research 153(2), 179-196.
Stacey et al (2015), Nature Communications 6, 6825.
Trichas et al (2008) BMC Biology 6, 40.
Usme-Ciro et al (2013) Virology Journal 10, 185.

The invention claimed is:

1. A method of treating a human subject suffering from a cancer comprising cells deficient in a caspase-dependent cell death pathway, the method comprising:
    (i) administering, intralesionally, to the human subject a replication-deficient recombinant virus for expression of interferon gamma in the human subject; and
    (ii) administering, intralesionally, to the human subject a therapeutically effective dose of Fluorouracil of about 0.02 mg/lesion to about 10 mg/lesion.

2. The method of claim 1, wherein the dose of Fluorouracil avoids induction of more than a moderate adverse event in the human subject.

3. The method of claim 1, wherein the recombinant virus is a recombinant DNA virus.

4. The method of claim 1, wherein the recombinant virus is a recombinant RNA virus.

5. The method of claim 1, wherein the recombinant virus is an adenovirus, an adeno-associated virus (AAV), a herpes simplex virus (HSV), a lentivirus, an Alphavirus, a Flavivirus, a Paramyxovirus, a Rhabdovirus, or a Orthomyxovirus.

6. The method of claim 1, wherein the recombinant virus is an adenovirus.

7. The method according to claim 1, further comprising administering one or more immune response-inducing or enhancing agents.

8. The method of claim 1, wherein the administrations are performed separately.

9. The method of claim 1, wherein the replication-deficient recombinant virus and the Fluorouracil are administered in a combined pharmaceutical composition comprising:
    (i) the therapeutically effective dose of Fluorouracil, and
    (ii) the recombinant virus.

10. The method of claim 1, wherein the cancer is selected from the group consisting of basal cell carcinoma, squamous cell carcinoma, and melanoma.

11. The method of claim 1, wherein the subject to be treated was identified as suffering from a cancer that is refractory or resistant to treatment with Fluorouracil alone.

12. The method of claim 1, wherein the cancer is basal cell carcinoma.

13. The method of claim 1, wherein the cancer is selected from the group consisting of colorectal cancer, breast cancer, colorectal cancer, ovarian cancer, cervical cancer, melanoma, non-melanoma skin cancer, gastric cancer, and pancreatic cancer.

14. A pharmaceutical composition for use in the treatment of a cancer comprising cells deficient in a caspase-dependent cell death pathway, the pharmaceutical composition comprising:

(i) a non-replicative recombinant virus for expression of interferon gamma in a human subject; and
(ii) about 0.02 mg/lesion to about 10 mg Fluorouracil, wherein the pharmaceutical composition is formulated for intralesional administration.

15. The pharmaceutical composition of claim 14, further comprising a controlled release matrix which comprises SiO2 matrix gel.

16. The pharmaceutical composition of claim 14, wherein the recombinant virus is an adenovirus.

\* \* \* \* \*